(12) United States Patent
Tol et al.

(10) Patent No.: US 10,589,106 B2
(45) Date of Patent: Mar. 17, 2020

(54) ELECTRONIC MODULE FOR A SYSTEM FOR NEURAL APPLICATIONS

(71) Applicant: Medtronic Bakken Research Center B.V., Maastricht (NL)

(72) Inventors: Jeroen Jacob Arnold Tol, Eindhoven (NL); Edward Willem Albert Young, Maastricht (NL); Egbertus Johannes Maria Bakker, Wijk en allburg (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 226 days.

(21) Appl. No.: 15/106,120

(22) PCT Filed: Jun. 20, 2014

(86) PCT No.: PCT/EP2014/063076
§ 371 (c)(1),
(2) Date: Jun. 17, 2016

(87) PCT Pub. No.: WO2015/090633
PCT Pub. Date: Jun. 25, 2015

(65) Prior Publication Data
US 2016/0317820 A1    Nov. 3, 2016

(30) Foreign Application Priority Data
Dec. 18, 2013   (WO) ................ PCT/EP2013/077085

(51) Int. Cl.
*A61N 1/375*    (2006.01)
*A61B 5/04*    (2006.01)
(Continued)

(52) U.S. Cl.
CPC ........ *A61N 1/3754* (2013.01); *A61B 5/04001* (2013.01); *A61B 5/0478* (2013.01);
(Continued)

(58) Field of Classification Search
CPC .............................. A61N 1/375; A61N 1/3754
(Continued)

(56) References Cited

U.S. PATENT DOCUMENTS 3,697,808 A   10/1972 Lee
5,559,500 A    9/1996 Kase
(Continued)

FOREIGN PATENT DOCUMENTS

EP         2745873 A1    6/2014
WO    2010055453 A1    5/2010
(Continued)

OTHER PUBLICATIONS

Gosselin et al., "A Mixed-Signal Multichip Neural Recording Interface With Bandwidth Reduction," IEEE Transactions on Biomedical Circuits and Systems, vol. 3, No. 3, Jun. 2009, pp. 129-141.
(Continued)

*Primary Examiner* — Carl H Layno
*Assistant Examiner* — Jon Eric C Morales
(74) *Attorney, Agent, or Firm* — Shumaker & Sieffert, P.A.

(57) ABSTRACT

An electronic module for a system for neural applications comprising a housing and a filtering element that form a closed, miniaturized Faraday cage a corresponding lead, active lead can, a controller and systems.

17 Claims, 7 Drawing Sheets

(51) Int. Cl.
  *A61N 1/05* (2006.01)
  *A61N 1/36* (2006.01)
  *A61B 5/00* (2006.01)
  *A61B 5/0478* (2006.01)

(52) U.S. Cl.
  CPC ............ *A61B 5/686* (2013.01); *A61N 1/0534* (2013.01); *A61N 1/3605* (2013.01)

(58) Field of Classification Search
  USPC ........................................................ 607/35
  See application file for complete search history.

(56) References Cited

U.S. PATENT DOCUMENTS

| | | | |
|---|---|---|---|
| 7,941,202 B2 | 5/2011 | Hetke et al. | |
| 2006/0173510 A1 | 8/2006 | Besio et al. | |
| 2006/0217782 A1 | 9/2006 | Boveja et al. | |
| 2007/0123766 A1* | 5/2007 | Whalen, III | A61B 5/04001 |
| | | | 600/395 |
| 2007/0217121 A1 | 9/2007 | Fu et al. | |
| 2008/0119906 A1* | 5/2008 | Starke | A61N 1/3754 |
| | | | 607/36 |
| 2008/0299381 A1* | 12/2008 | Zhang | A61N 1/0543 |
| | | | 428/315.9 |
| 2009/0259265 A1 | 10/2009 | Stevenson et al. | |
| 2010/0274319 A1 | 10/2010 | Meskens | |
| 2011/0009917 A1 | 1/2011 | Lavie | |
| 2013/0070423 A1 | 3/2013 | Iyer et al. | |

FOREIGN PATENT DOCUMENTS

| | | |
|---|---|---|
| WO | 2012018631 A2 | 2/2012 |
| WO | 2014095997 A1 | 6/2014 |
| WO | 2015090633 A1 | 6/2015 |

OTHER PUBLICATIONS

Gosselin et al., "Circuits techniques and microsystems assembly for intracortical multichannel ENG recording," IEEE 2009 Custom Intergrated Circuits Conference (CICC), Sep. 13-16, 2009, pp. 97-104.

International Search Report and Written Opinion from International Application No. PCT/EP2014/063076, dated Oct. 13, 2014, 8 pp.

U.S. Appl. No. 14/654,352, filed Dec. 18, 2013, by Jeroen Jacob Arnold Tol.

* cited by examiner

ELECTRONIC MODULE FOR A SYSTEM FOR NEURAL APPLICATIONS

BACKGROUND OF THE INVENTION

This application is a U.S. national stage entry of International Application No. PCT/EP2014/063076, filed Jun. 20, 2014, which claims the benefit of and priority from International Application No. PCT/EP2013/077085, filed Dec. 18, 2013, the entire contents of each of which are incorporated herein by reference.

SUMMARY OF THE INVENTION

The present invention relates to an electronic module for a system for neural applications, a lead for neural stimulation, a controller, an active lead can element 5 and a system for neural applications, especially a system for neurostimulation and/or neurorecording applications, for instance a deep brain stimulation system.

Implantable neurostimulation devices have been used for the past ten years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders (obsessive compulsive disorder, depression) are being researched and show promising results. In existing systems, the probes are connected to an implantable current pulse generator.

Currently, systems are under development with more, smaller electrodes in a technology based on thin film manufacturing. These novel systems consist of a lead made from a thin film based on thin film technology, as e.g. described in WO 2010/055453 A1. The thin film leads are fixed on a core material to form a lead. These probes will have multiple electrode areas and will enhance the precision to address the appropriate target in the brain and relax the specification of positioning. Meanwhile, undesired side effects due to undesired stimulation of neighbouring areas can be minimized.

Leads that are based on thin film manufacturing are e.g. described by U.S. Pat. No. 7,941,202 and have been used in research products in animal studies.

In existing systems, the DBS lead has e.g. four 1.5 mm-wide cylindrical electrodes at the distal end spaced by 0.5 mm or 1.5 mm. The diameter of the lead is 1.27 mm and the metal used for the electrodes and the interconnect wires is an alloy of platinum and iridium. The coiled interconnect wires are insulated individually by fluoropolymer coating and protected in an 80 micron urethane tubing. With such electrode design, the current distribution emanates uniformly around the circumference of the electrode, which leads to stimulation of all areas surrounding the electrode.

The lack of fine spatial control over field distributions implies that stimulation easily spreads into adjacent structures inducing adverse side-effects in about 30% of the patients. To overcome this problem, systems with high density electrode arrays are being developed, hence providing the ability to steer the stimulation field to the appropriate target.

The clinical benefit of DBS is largely dependent on the spatial distribution of the stimulation field in relation to brain anatomy. To maximize therapeutic benefits while avoiding unwanted side-effects, precise control over the stimulation field is essential.

During stimulation with existing DBS leads there is an option to use monopolar, bipolar, or even tripolar stimulation. Neurostimulator devices with steering brain stimulation capabilities can have a large number of electrode contacts (n>10) that can be connected to electrical circuits such as current sources and/or (system) ground. Stimulation may be considered monopolar when the distance between the anode and cathode is several times larger than the distance of the cathode to the stimulation target. During monopolar stimulation in homogeneous tissue the electric field is distributed roughly spherical similar to the field from a point source. When the anode is located close to the cathode the distribution of the field becomes more directed in the anode-cathode direction. As a result the field gets stronger and neurons are more likely to be activated in this area due to a higher field gradient.

The mechanisms of DBS are unknown. However, it is hypothesized that polarization (de- and/or hyperpolarization) of neural tissue is likely to play a prominent role for both suppression of clinical symptoms, as well as induction of stimulation-induced side-effects. In order to activate a neuron it has to be depolarized. Neurons are depolarized more easily close to the cathode than by the anode (about 3-7 times more depending on type of neuron, etc.).

Therefore, compared to monopolar stimulation the effect of bipolar stimulation is less spread of the electric field, a stronger electric field between the anode and cathode, and more activated neurons close to the cathode. Bipolar stimulation is therefore used to focus the field to certain areas in cases when beneficial stimulation is not obtained during monopolar stimulation.

DBS leads are typically implanted via a stereotactic neurosurgical procedure. The planning of a stereotactic procedure involves the identification of the DBS target (e.g. the subthalamic nucleus) on the basis of the MR or CT images of the patient's head/brain and defining a point within the target nucleus. Eventually the stereotactic planning station (e.g. a computer system) provides the stereotactic coordinates of the target point. The stereotactic coordinates can be referenced externally and thus be used in the operating room to precisely navigate the DBS lead to the selected point in the brain.

To reduce the clinical impact of the implanted parts on a patient, a miniaturization of the components of the DBS system like the implantable pulse generator and e.g. the active lead can element comprising electronic parts of the DBS system is not only desirable but also mandatory. The active lead can element has strict size requirements to reduce its clinical impact, for example skin erosion, when the active lead can element is mounted on a patient's skull. The implantable pulse generator cannot be made too large either, although desired from a battery longevity point of view, because of patient comfort and displacement risk if the implantable pulse generator size and weight is made too large.

Another drawback of existing implanted electronic systems is that any electromagnetic interference (EMI) is only sufficiently kept outside the area of the active lead can that is vulnerable to EMI at the cost of a large volume increase of the module.

The techniques to shrink the active lead can element can also advantageously be applied to the implantable pulse generator, or any other implant module, for example, to trade for an increase in battery volume to extend its capacity and/or for increasing the functionality of the implantable pulse generator.

It is therefore an object of the present invention to improve an electronic module for a system for neural applications, a lead for neural stimulation, a controller, an active lead can element and a system for neural applications.

In one aspect a reduction of the passive electronic components volume and area claim of at least a part of the electronics of a system for neural applications is provided.

In another aspect, a lead for neural stimulation, a controller, an active lead can element and a system for neural applications, which are less vulnerable to EMI.

According to a first aspect there is an electronic module for a system for neural applications, especially a neurostimulation and/or neurorecording system, further especially a deep brain stimulation (DBS) system, wherein the electronic module comprises at least one integrated passive device.

By this, the advantage is achieved that a reduction of the passive electronic components volume and area claim of at least a part of the electronics of a system for neural applications can be provided.

In particular, a significant reduction of the dominant volume claim of passive electrical components and networks of an implant can be achieved with the application of integrated passive devices, also referred to as integrated passive components. This integration brings the passives volume claim in line with the achievable mechanical miniaturization leading to maximum shrinkage of the volume and area of a system for neural applications.

Filters and DC blocking capacitors are the discrete components that claim most volume and area in the active lead can because of the large number of connections of the active lead can electronics with the outside world, and therefore, with a high number of feed-through pins. A reduction of the passives volume and area claim is essential to meet the strict size requirements of the electronics of a system for neural applications, which can be achieved by integration of the passives into a single module.

This passives integration can be achieved with various integrated passive device technologies. Capacitor modules with an array of multilayer ceramic capacitors are available on the market. Integration of different types of passives (resistors, capacitors and inductors) with one or more interconnect layers using thin or thick film technology to realize the integration of multiple passives on a common ceramic substrate is quite common. Recently, integrated passive devices with several integrated capacitors and interconnections on a silicon chip have also become available.

Integrated passive devices or integrated passive components are attracting an increasing interest due to constant needs e.g. of handheld wireless devices to further decrease in size and cost and increase in functionality. Many functional blocks such as impedance matching circuits, harmonic filters, couplers and baluns and power combiner/divider can be realized by integrated passive devices technology. Integrated passive devices can be designed as flip chip mountable or wire bondable components and the substrates for integrated passive devices usually are thin film substrates like silicon, alumina or glass.

Integrated passive devices are generally fabricated using standard screen print technology on ceramic or standard wafer fab technologies on silicon such as thin film and photolithography processing. Alternatively, modules can be manufactured from green foil e.g. with Low Temperature Co-fired Ceramic technology. DC blocking capacitors are often applied in implantable medical devices such as a system for neural applications in order to prevent e.g. DC leakage currents. Those and other passive components can be integrated on an integrated passive device, for example, to save precious implant volume and/or increase component reliability, which becomes attractive if many passives are needed. Recently, the DC blocking capacitors can also be realized in an integrated passive device where the capacitors are integrated on a silicon chip, for example, 3D capacitors in a common substrate.

For this type of integrated passive device, if a DC bias voltage is applied to prevent forward biasing of the capacitor-substrate diodes during normal operation, a failure of the integrated passive device can give rise to tissue leakage current. For example, if the DC blocking capacitors are directly connected to e.g. a stimulation and/or recording electrode lead, an integrated passive device failure might short the DC biased integrated passive device chip substrate to one or more lead electrodes directly. This failure might lead to unwanted and potentially hazardous tissue DC leakage current. Advantageously, due to the use or provision of a leakage current detection and/or prevention means the integrated passive device can be biased safely.

The electronic system may be an electronic system for a system for neural applications or, more specifically for brain applications, preferably for a neurostimulation and/or neurorecording system. Such a neurostimulation and/or neurorecording system may be e.g. a DBS system.

The lead may e.g. comprise at least one thin film, whereby the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or merely the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

The active lead can element may comprise electronic means to address the plurality of electrodes and at least one active lead can connecting means. Further, the active lead can element may be hermetically or merely hermetically sealed and may comprise electronic means to address the plurality of electrodes on the distal end of the thin film, which is arranged at the distal end and next to the distal tip of the lead. The plurality of electrodes may comprise 5-10 or more electrodes, e.g. 16 or 32 electrodes, or in preferred embodiments e.g. 40 electrodes or more. The electrodes may be arranged such that the electrodes are merely evenly distributed arranged all over the distal end of the lead.

The active lead can element may be e.g. basically a multi-pin connector with a low-count feed-through (LCFX) connector with e.g. five pins for the interface cable e.g. between active lead can element and implantable pulse generator and another high-count feed-through (HCFX) connector with e.g. 40 pins for the lead.

Any other suitable number of pins for the LCFX and HCFX may be also used if needed.

For instance, it is mechanically possible to design these two feed-through connectors with a high pin density to reduce the active lead can element area significantly. However, this area advantage can only materialize if the electrical components of the active lead can element can be shrunk in similar proportions as the feed-through connectors, which is now advantageously possible according to the invention. Moreover, e.g. a very thin active lead can element, most desirable to reduce its impact on skin erosion, not only requires a high pin density but also a reduction in the height of both feed-through pins and interior electrical components. Thus both the active lead can element electronics volume and area must be miniaturized to realize a small active lead can element. The techniques to shrink the active lead can element can also advantageously be applied to the implantable pulse generator, or any other implant module, for example, to trade for an increase in battery volume to extend its capacity and/or for increasing the functionality of the implantable pulse generator.

Furthermore, it is possible that the electronic module comprises at least one filtering element, wherein the filtering element is exemplarily a feed-through filter, and/or at least one blocking element, wherein the blocking element is exemplarily a DC blocking element and/or at least one application specific integrated circuit (ASIC).

Especially, it is possible that the integrated passive device comprises the at least one filtering element, wherein the filtering element is exemplarily a feed-through filter, and/or the at least one blocking element, wherein the blocking element is exemplarily a DC blocking element.

It is for instance possible that the filtering element is realized in a first integrated passive device and that the blocking element is realized in a second integrated passive device.

The filtering element and/or the blocking element and/or the ASIC may be stacked one upon the other. The stack may be a thin stack and a low volume. The filtering can be provided by any means which is/are capable to provide a filtering. In particular, a filtering can be provided by any passive means or passive network.

The filtering element may be configured such that interferences, in particular unwanted interferences e.g. caused by mobile phones or the like, can be removed before they may enter e.g. a part of the housing of the system for neural applications. Thereby, the advantage is achieved that a protection against electromagnetic interference (EMI) is provided, for example, against mobile phone induced fields while the patient is using its mobile phone. The filtering element may be or may comprise e.g. an RF feed-through filter. The filter may comprise e.g. a capacitor, a coil, an inductor, a resistor or any other suitable passive component.

The blocking element may be configured such that in the event of a leakage current such leakage current, in particular DC leakage current flow is prevented. Regulations demand that (almost) no DC current flows through the patient carrying an implant such as a deep brain stimulator, even when a (single) failure occurs of, for example, the implant's electronics. This DC leakage design problem is solved by the application of DC blocking capacitors. Again, with a high number of feed-through pins, it becomes mandatory to integrate those blocking capacitors to achieve a minimum volume and area claim as opposed to the application of discrete components.

The ASIC may comprise a part or e.g. all active electronics with some external passives, for example, power supply decoupling capacitors. A substrate with integrated passives (resistors, capacitors and inductors) may be used as substrate for off-chip (rerouting to) an ASIC and together a so called hybrid or hybrid integrated circuit may be realized. By the use of one or more ASICs the active electronic components of at least a part of the system for neural application may be miniaturized.

Mechanical miniaturization of an implant module really pays off if all of its interior electrical components can be shrunk to the same extent. Active electronics can be miniaturized by integration on one or more ASIC dies but the largest part of an implant's volume is often claimed by the external (passive) components and networks that cannot be integrated into the ASIC because 1. it is technologically not feasible, for example, the integration of inductors or capacitors with large values cannot be integrated on-chip;

2. it is too costly, because the desired components, for example, hundreds of nano Farad DC blocking capacitors, consume too much chip area;

3. it is functionally undesired or ineffective to put the passives on the ASIC die, for example, feed-through filters are only effective when put close to and/or integrated with the feed-through pins, while DC blocking capacitors should electrically be isolated from the active electronics by integration on a separate die and/or substrate.

The volume and area claim of the passive components is especially high if feedthrough connectors have a high pin density and feed-through filter networks are required. However, by the combination of integrated passive devices and one or more ASICs the advantage can be achieved that not only the active electronics can be shrunk due to the use of ASICs but also the passive electronics can be shrunk due to the use of integrated passive devices.

Moreover, it is possible that the integrated passive device comprises and/or is connected and/or connectable to several sections of interconnects e.g. one or more low-count feed-through pins and/or one or more high-count feed-through pins and/or an ASIC and/or another integrated passive device and/or at least one bias terminal, especially wherein the in- and/or output of the integrated passive device is connected to the filtered out- and/or input via at least one capacitor and/or at least one resistor and/or at least one inductor, and/or that the integrated passive device comprises a substrate and/or at least one diode and at least one passive electronic component which is arranged on and/or in the substrate.

The filtering of the filtered out- and/or input may be provided by the at least one filtering element.

Additionally, it is possible that the electronic module comprises at least one first connector element, e.g. the LCFX connector, and at least one second connector element, e.g. the HCFX connector, the first connector element being configured such that the electronic module is directly and/or indirectly connectable or connected to a controller, e.g. the integrated passive device, which is at least configured to supply and/or provide and/or measure at least one voltage and/or at least one current and/or at least one voltage waveform and/or at least one current waveform especially via one or more stimulation and/or recording and/or clock and/or power and/or communications outputs and/or inputs, the second connector element being configured such that the electronic module is directly and/or indirectly connectable or connected to a lead for neural stimulation and/or recording and/or the electronic module is directly and/or indirectly connectable or connected to an active lead can element and/or directly and/or indirectly connectable or connected to a housing.

The electronic module and/or its components advantageously make sure that, to the largest extent possible, any electromagnetic interference (EMI) is kept outside the area of the active lead can that is vulnerable to EMI, while EMI generated inside the active lead can is also prevented to radiate to the outside. A conductive (e.g. titanium) housing is used to achieve this electromagnetic shielding with the electromagnetic opening, formed by the (non-conductive) ceramic with the embedded LCFX and HCFX pins, being electromagnetically closed by the feed-through filtering element of the electronic module. This filtering element, exemplarily an array of feed-through capacitors, redirects the EMI currents to the (conductive) housing.

Furthermore, it is possible that the integrated passive device comprises one or more passive electronic components, especially at least one capacitor and/or at least one inductor and/or one diode and/or at least one substrate terminal, further especially only capacitors and/or inductors and/or diodes and/or at least one substrate terminal, especially only one or more passive electronic components, especially at least one capacitor and/or at least one inductor and/or at least one diode and/or at least one substrate terminal, further especially only capacitors and/or inductors and/or diodes and/or at least one substrate terminal.

Moreover, the electronic system comprises exemplarily at least one biasing means.

If the integrated passive device has its components embedded in and/or integrated on a common (silicon) chip substrate, the substrate may need to be biased with a voltage that is lower (for a p-type substrate but higher for an ntype substrate) than the lowest (highest for n-type substrate) voltage ever appearing on the in- and/or output terminals of the integrated passive device so that all component-substrate junctions remain reversed biased during normal operation. Otherwise unwanted substrate currents are injected into the integrated passive device, and therefore, into the integrated passive device components. Thus this type of integrated passive device, whose components share a common conductive substrate, can be provided with a DC voltage to bias its substrate correctly. Especially (substrate) diodes of the integrated passive device may be biased, respectively reverse biased.

Moreover, it is possible that the integrated passive device comprises one or more feed-through capacitors which are mounted on and/or integrated into a substrate, in particular a ceramic substrate and/or one or more integrated DC blocking capacitors which are mounted on and/or integrated into a substrate, in particular a silicon substrate. Alternatively, the integrated passive component is manufactured from a flexible organic capacitor in a flex foil and/or PCB, and/or a (screen) printed capacitor on a ceramic substrate, and/or a capacitor built using thick film on ceramic technology, and/or a capacitor that is built on a ceramic substrate using physical vapor deposition (PVD), and/or a stack of ceramic substrates with a (screen) printed thick film capacitor, in particular a capacitor built using low temperature co-fired ceramic (LTCC) technology, and/or a 3D-in-silicon capacitor.

The integrated passive component may also be manufactured from a metalinsulator-metal (MIM) capacitor on silicon technology.

The one or more feed-through capacitors may be a part of the feed-through filter. The feed-through capacitors may be (screen) printed e.g. on the top side of the substrate of the integrated passive device. The capacitors may be made of a sandwich of two (or more) conductive layers with a (relatively) high-k dielectric in between. The one or more integrated DC blocking capacitors may be a part of the at least one blocking element.

Also, it is possible that the substrate comprises a contact surface portion, especially a ground plane on the substrate top, which is directly and/or indirectly electrically (e.g. galvanically, ohmically) and/or capacitively connected to a (conductive) housing of the electronic module, especially via a ring of conductive adhesive, preferably conductive adhesive epoxy, so that the feed-through capacitors and the housing together form a (high-frequency) closed, miniaturized Faraday cage only penetrated by through-hole substrate vias that are capacitively and/or electrically, in particular galvanically, coupled to the Faraday cage.

The housing of the electronic module may be a conductive housing, for example, a titanium housing. A metal housing combines mechanical protection of the module with electromagnetic shielding. Alternatively, a metalized polymer can be used for mechanical protection and electromagnetic shielding.

By this, the advantage is achieved that, to the largest extent possible, any electromagnetic interference (EMI) is kept outside the area of the active lead can that is vulnerable to EMI, while EMI generated inside the active lead can is also prevented to radiate to the outside. Each feed-through pin may connect to the top contact (e.g. a gold top contact) of a single capacitor in the array of the feed-through capacitors (e.g. a thick film capacitor array) via stud bumps. Through-hole signal vias may connect the feed-through pins to one or more interconnect layers on the bottom side of the substrate. Each metal layer can have a maximum area fill factor so that a maximum overlap between all metal layers is achieved, increasing the capacitance per printed dielectric layer, and forming a (high-frequency) closed Faraday cage with the (conductive) housing of the module.

Thus a minimum spacing between the individual top contacts and a minimum spacing between the through-hole vias and the ground plane increase the filter's efficacy, because it increases the capacitance per pin and more importantly, it minimizes the openings in the metal layers. If desired, an additional ground layer can be applied to electrically close the filter's 3D structure further. Further, the mutual ground plane of all array capacitors may extend beyond the capacitor arrays itself and may be connected with a ring of ground vias to the other side of the substrate to provide ground to the interior of the ALC. Alternatively or additionally, the top and bottom substrate ground planes can be connected via metallization wrapped around the substrate's side edges. So, the ground plane on the substrate top is electrically connected to a (conductive) housing of the electronic module via a ring of conductive adhesive, especially conductive adhesive epoxy, so that the feed-through capacitors and the housing together form a (high-frequency) closed, miniaturized Faraday cage only penetrated by the through-hole substrate vias from which EMI currents are diverted through feed-through capacitors to the (conductive) housing before they can enter the housing. The other way around, this embedding of the feed-through filter in the (conductive) housing guarantees, to the largest extent possible, that any EMI generated inside the active lead can is also prevented to radiate to the outside.

Furthermore, it is possible that the substrate comprises holes, wherein through-hole signal vias connect the feed-through pins to one or more interconnect layers on the bottom side of the substrate.

Additionally, it is possible that the electronic module comprises at least partially a multi-layer structure, wherein especially the filtering element forms a first layer and/or the blocking element forms a second layer and/or the ASIC forms a third layer.

By this multi-layer structure the advantage is achieved that all or almost all electrical and electronic components fit in a very small volume and area.

Moreover, it is possible that the module comprises a dedicated routing substrate and/or an already available substrate for routing for passive components and/or active components which are mounted outside an integrated passive device, in particular for at least one discrete component, e.g. a surface mounted device (SMD).

The routing substrate may be the substrate which carries the DC blocking elements, in particular the DC blocking capacitors.

More efficient filtering, for example better EMI suppression, can be realized with a combination of passive components, capacitors, resistors and inductors. Further, it is possible that the integrated passive device, for example realizing the feed-through filtering element, comprises at least one resistor, especially a series resistor, and/or an inductor, especially a series inductor, and/or a capacitor, especially a parallel capacitor, wherein the resistor and/or the inductor and/or the capacitor is/are configured such that a (parasitic) filter resonance may be dampened and/or the filter's suppression, especially the suppression of electromagnetic interference, may be improved and/or increased.

For example, a series resistor and/or an inductor and/or a capacitor can be added to dampen any (parasitic) filter resonances and/or to increase the (series) impedance of the filtering element towards the electronics it is connected to. By this, the (high-frequency) shorting efficacy of the filter to the housing may be improved.

Also, the present invention relates to a lead. Accordingly, a lead is provided, the lead being a lead for neural stimulation comprising at least one electronic module for a system for neural applications according to any of the previously mentioned aspects.

Furthermore, the present invention relates to a controller. Accordingly, a controller is provided, especially an implantable pulse generator comprising at least one electronic module for a system for neural applications according to any of the previously mentioned aspects.

Additionally, the present invention relates to an active lead can element. Accordingly, an active lead can element comprises at least one electronic module for a system for neural applications according to any of the previously mentioned aspects.

Moreover, the present invention relates to a system for neural applications. Accordingly, a system for neural applications is provided, especially a system for neurostimulation and/or neurorecording applications, especially a deep brain stimulation system. The system for neural applications comprises at least one electronic module for a system for neural applications and/or comprises at least one lead and/or comprises at least one controller and/or comprises at least one active lead can element according to any of the previously mentioned aspects.

In an aspect of the invention an electronic module for a system for neural applications is provided that comprises a housing and a filtering element that form a (high-frequency) closed, miniaturized Faraday cage.

A miniaturized Faraday cage may be understood as being formed by a housing with an overall thickness of less than approx. 10 mm, especially less than approx. 5 mm, further especially less than approx. 4 mm or 3 mm.

For example, the dimension of the housing can be e.g. less than approx. 20 mm length, less than approx. 10 mm width and as already mentioned of a thickness with less than approx. approx. 10 mm, especially less than approx. 5 mm, further especially less than approx. 4 mm or 3 mm.

The housing may be formed of an electrically conductive material, as for example titanium. According to this aspect of the invention, the Faraday cage may be formed by a combination of the housing and the filtering element.

Advantageously, the filtering element forms an integral part of the housing. The filtering element can be configured as a feed-through filter. The filtering element can be configured as an electromagnetic interference (EMI) filter, in particular as EMI feed-through filter. In this regard, the filtering element can comprise filter capacitors, in particular feed-through capacitors. The housing has at least one portion which is not entirely or sufficiently closed by conductive material, i.e. the housing has at least one portion comprising at least partially material that is not electrically conductive (for example ceramic) and/or has insulating properties. Generally speaking it is possible that the conductive housing may be only penetrated by through-hole substrate vias/pins that are electrically isolated from this housing. The at least one portion of the housing comprising non-conductive material can be due to feed-through pins. The feed through pins can be capacitively coupled to the housing. The Faraday cage is closed by the EMI filter with respect to the at least one portion of the housing comprising non-conductive material.

The filtering element may comprise a substrate or may be realized on a substrate or may be integrated into a substrate.

In particular, the filtering element can comprise a substrate that is configured to close the Faraday cage with respect to the at least one portion of the housing comprising non-conductive material. The filtering element can comprise an electrically conductive layer, in particular an electrically conductive plane or plate that is configured to close the Faraday cage with respect to the non-conductive area of the housing. The filtering element is therefore advantageously arranged in and close to the area (portion) where the housing is insufficiently closed by conductive material. The capacitors and/or filters and/or complete filter structures can be coupled with one side to the electrically conductive layer.

The conductive layer can be a ground plate/plane of the substrate, in particular a common ground plane of the capacitors. For example, the ground plate/plane may be connected to the housing.

Furthermore, the ground plate/plane may be have a different potential as the electronics module system ground (GND), i.e. the ground plate/plane can be connect to system ground (GND), but this is not mandatory for the Faraday cage to function properly.

The conductive layer can then be electrically and/or capacitively, in particular galvanically coupled to the conductive housing. Advantageously, the conductive layer (substrate) is designed to cover most of the at least one area or portion where the housing is insufficiently closed in terms of a Faraday cage.

The substrate and conductive layer is advantageously only interrupted by very small holes or areas for vias leading/penetrating through the substrate.

A plate (which is also a conductive layer) of the capacitors can then advantageously be arranged such that it at least partially overlaps an area without the other conductive layer due to the substrate vias.

The other conductive layer can overlap the areas free of the main conductive layer (e.g. the ground plane) due to substrate vias. This configuration basically (electrically) closes the gaps in the main conductive layer due to vias. In other words, gaps in a first conductive layer (e.g. ground plane) due to vias are closed by a second conductive layer which is electrically (galvanically, ohmically) isolated from the first layer. This second conductive layer can advantageously be a plate of a feed-through capacitor.

Furthermore, the plate of the feed-through capacitor can then also serve as contact area (pad, stud bumps, bondable area/pad) for connecting feed-through pins entering the housing. So, the Faraday cage is formed by the housing itself and the conductive continuous ground plane that is glued to the housing. The continuous ground plane (first conductive layer) has gaps/holes for the through-hole signal vias, as signals have to be brought to the inside of the electronic module (e.g. active lead can). Thus, these holes form openings in the otherwise electrically closed Faraday cage. In order to prevent EMI currents from entering the inside of the electronic module via these signal vias, capacitors (or more generally the EMI filter(s)) are connected between each incoming feed-through pin and the housing (via the ground plane (first conductive layer) glued to the housing) to divert EMI currents to the housing. In this way, the Faraday cage is electrically closed again (by a second conductive layer which can also serve as connecting stud bumps for the feed-through pins) despite the openings in the ground plane and the through-hole signal vias to the inside of the electronic module. The feed-through pins themselves can be held together by a non-conductive ceramic 563. This non-conductive ceramic leads to openings in the (titanium) housing for EMI and is one example of the non-conductive material. The ground plane (first conductive layer) on the substrate top advantageously forms the common bottom plate of many, most or all feed-through capacitors (or more generally the EMI filter(s)). The capacitors may be e.g. part of a larger EMI filter.

In other words, this aspect of the invention benefits from the realization of a thin EMI filter on a substrate. The filter can advantageously be manufactured in thin and/or thick film technology. The application and design of this substrate form a miniaturized Faraday cage (i) by the way the EMI filter is constructed, namely a ground plane that extends to the substrate's edges and is penetrated by small holes for the signal vias only, (ii) by galvanically connecting this substrate or more specifically its ground plane to the housing with conductive material, like for example conductive epoxy, and (iii) by preventing signals to enter the inside of the electronic module through the signal vias by diverting any EMI currents via the EMI filter or EMI filter capacitors to the housing.

This means that the Faraday cage can be formed by the housing and the chosen design of the EMI filter or filter capacitors (for example FX EMI filter or FX filter capacitors or more specifically a FX EMI filter integrated with the rest of the Faraday cage enclosure). More specifically the Faraday cage can be formed by the ground plate that all capacitors have in common and which is glued to the conductive titanium housing.

According to aspects of the invention, a filter (filtering element) is applied, preferably as an integral part of the Faraday cage, to divert the high-frequency EMI to the housing i.e. outside of the Faraday cage while passing the intended low(er)-frequency signals to the electronics inside of it.

The ground plane may comprise the contact surface portion, especially wherein the ground plane may comprise the contact surface portion on the substrate top. The contact surface portion may be connected to the housing of the electronic module, so that the feed-through capacitors and the housing together form the (high-frequency) closed, miniaturized Faraday cage.

The contact surface portion can be connected to the housing electrically and/or galvanically and/or capacitively. The contact surface portion can be a ground plane on the substrate top. The contact surface portion can be connected to the housing via a ring of conductive adhesive. The conductive adhesives can be conductive adhesive epoxy. All these aspects advantageously contribute to less vulnerability to EMI.

The substrate can comprise holes, wherein through-hole signal vias can connect the feed-through pins to one or more interconnect layers on the bottom side of the substrate.

The electronic module configured as a Faraday-cage can comprises at least one filtering element as previously described. The electronic module can further comprise at least one blocking element. The filtering element can be a feed-through filter. The blocking element can be a DC blocking element.

The electronic module configured as a Faraday-cage can comprise several sections of interconnects such as one or more low-count feed-through pins and/or one or more high-count feed-through pins.

The electronic module configured as a Faraday cage can comprise an ASIC and/or another integrated passive device and/or at least one bias terminal.

The electronic module configured as a Faraday cage can be connected or connectable to several sections of interconnects such as one or more low-count feed-through pins and/or one or more high-count feed-through pins.

The electronic module configured as a Faraday cage can comprise at least one first connector element and at least one second connector element.

The first connector element can be configured such that the electronic module is connectable or connected to a controller which is at least configured to supply or provide at least one electrical signal.

The electronic module configured as a Faraday cage can comprise at least one first connector element and at least one second connector element, the first connector element being configured such that the electronic module is connectable or connected to a controller which is at least configured to measure at least one electrical signal. The second connector element can be configured such that the electronic module is connectable or connected to a lead for neural stimulation and/or recording. The second connector element can be configured such that the electronic module is connectable or connected to an active lead can element and/or to a housing. The electrical signal can include at least one voltage and/or at least one current and/or at least one voltage waveform and/or at least one current waveform. The controller can be configured to supply or provide the electrical signal via at least one output and/or to measure the electrical signal via at least one input. The output can be a stimulation and/or clock and/or power and/or communications output. The input can be a recording and/or power and/or clock and/or communications input.

In connection with the recording input it is explicitly mentioned that the ASIC may amplify via a connector element analog neural signal into digital data that are sent to a controller, e.g. an IPG. This can be done e.g. via a communication interface line.

With respect to the above described configuration of the Faraday cage, the first connector and/or the second connector and the respective feed-through pins of the connector form the portion(s) and or area(s) of the housing of the electronic module which are advantageously covered by the substrate, in particular covered by the conductive layer(s) of the substrate of the filtering element. The filtering element can then advantageously be arranged beneath the first connector and/or the second connector. An arrangement where the filtering element, in particular the substrate of the filtering element and more specifically the conductive layer of the substrate overlaps (or extends over) the outer edge of the first and/or second connector in order to fully cover the area of the connector(s). This can also allow the contact surface portion of the filtering element to be galvanically coupled to the housing.

Furthermore, the filtering element, the substrate of the filtering element, and/or the conductive layer (or several conductive layers) of the filtering element are configured such the conductive areas (pads, stud bumps, gold contacts) coincide with interconnecting areas of feed-through pins of the first connector and/or second connector. This allows the filtering element to be placed and connected directly beneath the first connector and/or second connector.

The substrate can be a ceramic substrate or a silicon substrate.

The electronic module can comprise at least partially a multi-layer structure. The filtering element can then form a first layer. The blocking element can form a second layer. The application specific integrated circuit (ASIC) can forms a third layer.

The module can comprise a dedicated routing substrate and/or an already available substrate for routing for passive components.

The filtering element can comprise at least one passive component, however, typically there are more passive components arranged on or in the filtering element.

The passive component can be at least one discrete component such as a surface mounted device (SMD). The passive component can also be a thin or thick film element or an integrated component.

The passive component can be at least one out of a resistor and an inductor and a capacitor. The resistor and/or the inductor and/or capacitor can be configured such that a (parasitic) filter resonance may be dampened. The resistor and/or the inductor and/or capacitor can be configured such that the filter's suppression such as the suppression of electromagnetic interference may be improved or increased. The resistor can be a series resistor and/or the inductor can be a series inductor and/or the capacitor can be a parallel capacitor.

The invention also provides a lead for neural stimulation comprising at least one electronic module configured as a Faraday cage for a system for neural applications according to the previously mentioned aspects.

The electronic module configured as a Faraday cage can be configured as an implant or implantable device of any kind. Advantageously, the electronic module can also be an implantable pulse generator.

The invention further provides a controller comprising at least one electronic module configured as a Faraday cage for a system for neural applications. The controller can be an implantable pulse generator. The invention further provides an active lead can element comprising at least one electronic module configured as a Faraday cage for a system for neural applications. The invention also provides a system for neural applications comprising at least one electronic module configured as a Faraday cage for a system for neural applications and/or comprising at least one lead and/or comprising at least one controller and/or comprising at least one active lead can element according the previously mentioned aspects.

An electronic module, the controller, the active lead can element and/or the system can particularly be configured for a neurostimulation and/or neurorecording system and/or a deep brain stimulation (DBS) system.

As already mentioned above, it is possible that the substrate comprises a contact surface portion, especially a ground plane on the substrate top, which is directly and/or indirectly electrically and/or capacitively and/or galvanically connected to a (conductive) housing of the electronic module, especially via a ring of conductive adhesive, preferably conductive adhesive epoxy, so that the feed-through capacitors and the housing together form a (high-frequency) closed, miniaturized Faraday cage only penetrated by (through-hole) signal substrate vias that are capacitively and/or electrically coupled to the Faraday cage.

The housing of the electronic module may be a conductive housing, for example, a titanium housing. A metal housing combines mechanical protection of the module with electromagnetic shielding. Alternatively, a metalized polymer can be used for mechanical protection and electromagnetic shielding.

By this, the advantage is achieved that, to the largest extent possible, any electromagnetic interference (EMI) is kept outside the area of the active lead can that is vulnerable to EMI, while EMI generated inside the active lead can is also prevented to radiate to the outside. Each feed-through pin may connect to the top contact (e.g. a gold top contact) of a single capacitor in the array of the feed-through capacitors (e.g. a thick film capacitor array) via stud bumps. Through-hole signal vias may connect the feed-through pins to one or more interconnect layers on the bottom side of the substrate. Each metal layer can have a maximum area fill factor so that a maximum overlap between all metal layers is achieved, increasing the capacitance per printed dielectric layer, and forming a (high-frequency) closed Faraday cage with the (conductive) housing of the module.

Thus a minimum spacing between the individual top contacts and a minimum spacing between the through-hole vias and the ground plane increase the filter's efficacy, because it increases the capacitance per pin and more importantly, it minimizes the openings in the metal layers. If desired, an additional ground layer can be applied to electrically close the filter's 3D structure further. Further, the mutual ground plane of all array capacitors may extend beyond the capacitor arrays itself and may be connected with a ring of ground vias to the other side of the substrate to provide ground to the interior of the ALC. Alternatively or additionally, the top and bottom substrate ground planes can be connected via metallization wrapped around the substrate's side edges. So, the ground plane on the substrate top is electrically connected to a (conductive) housing of the electronic module via a ring of conductive adhesive, especially conductive adhesive epoxy, so that the feed-through capacitors and the housing together form a (high-frequency) closed, miniaturized Faraday cage only penetrated by the through-hole substrate vias from which EMI currents are diverted through feed-through capacitors to the (conductive) housing before they can enter the housing. The other way around, this embedding of the feed-through filter in the (conductive) housing guarantees, to the largest extent possible, that any EMI generated inside the active lead can is also prevented to radiate to the outside.

BRIEF DESCRIPTION OF THE DRAWINGS

Further details and advantages of the present invention shall be described hereinafter with respect to the drawings.

DETAILED DESCRIPTION

Figure 1:
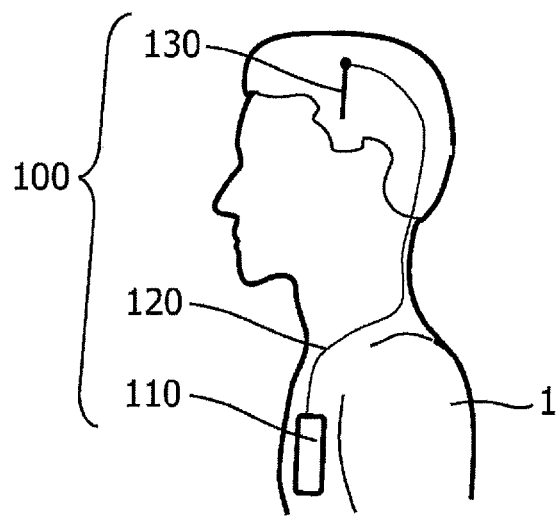
FIG. 1: a schematical drawing of a neurostimulation system for deep brain stimulation (DBS)

A possible embodiment of a neurostimulation system 100 for deep brain 25 stimulation (DBS) is shown in FIG. 1. The neurostimulation system 100 comprises at least a controller 110 that may be surgically implanted in the chest region of a patient 1, typically below the clavicle or in the abdominal region of a patient 1. The controller 110 can be adapted to supply the necessary voltage pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

Figure 2:
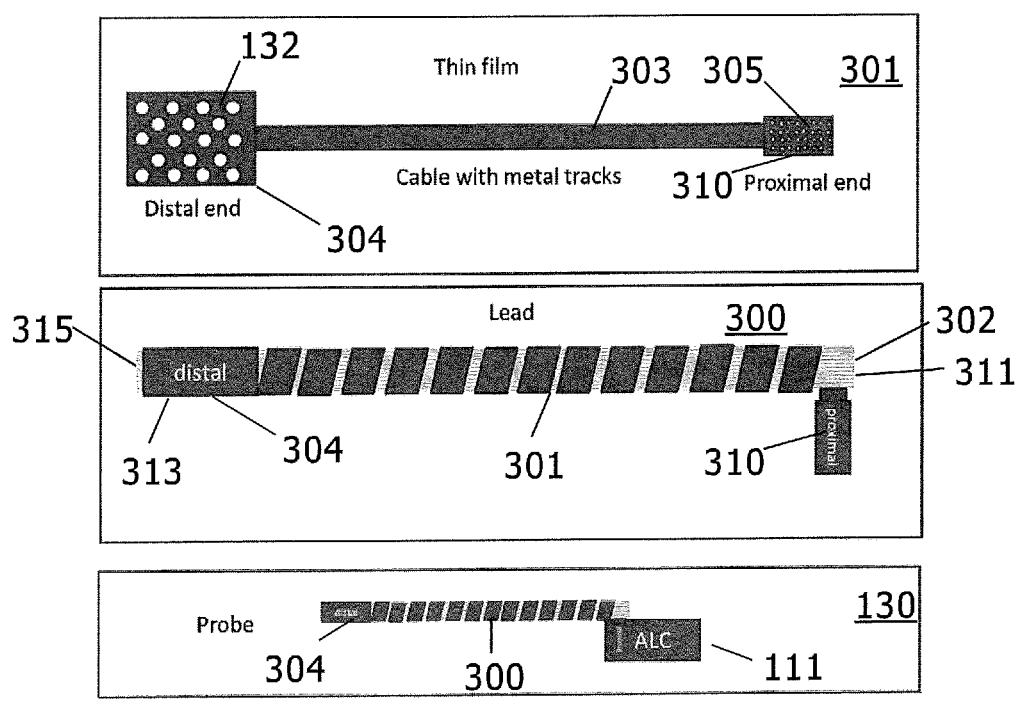
FIG. 2: a further schematical drawing of a probe of a neurostimulation system for deep brain stimulation (DBS) and its components.

FIG. 2 further illustrates a typical architecture for a Deep Brain Stimulation probe 130 that comprises a DBS lead 300 and an active lead can element 111 comprising electronic means to address electrodes 132 on the distal end 304 of the thin film 301, which is arranged at the distal end 313 and next to the distal tip 315 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 arranged at the proximal end 311 of the lead 300 is electrically connected to the active lead can element 111. The active lead can element 111 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises metal lines (not shown) to connect each distal electrodes 132 to a designated proximal contact 305.

Figure 3:
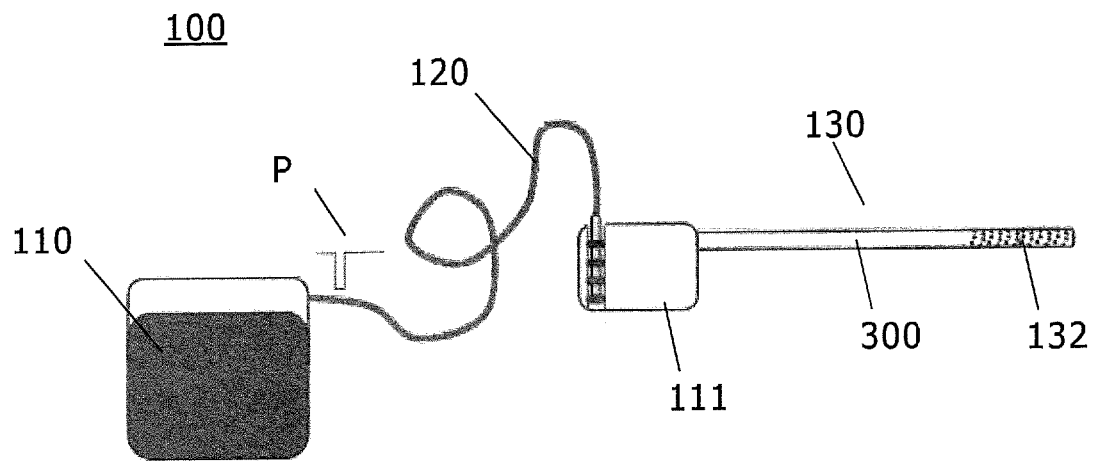
FIG. 3: a schematical drawing of a probe system according to the present invention.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, wherein e.g. 40 electrodes 132 can be provided on outer body surface at the distal end of the probe 130. By means of the extension wire 120 pulses P supplied by controller 110 can be transmitted to the active lead can 111. The controller 110 can be an implantable pulse generator 110.

Figure 4:
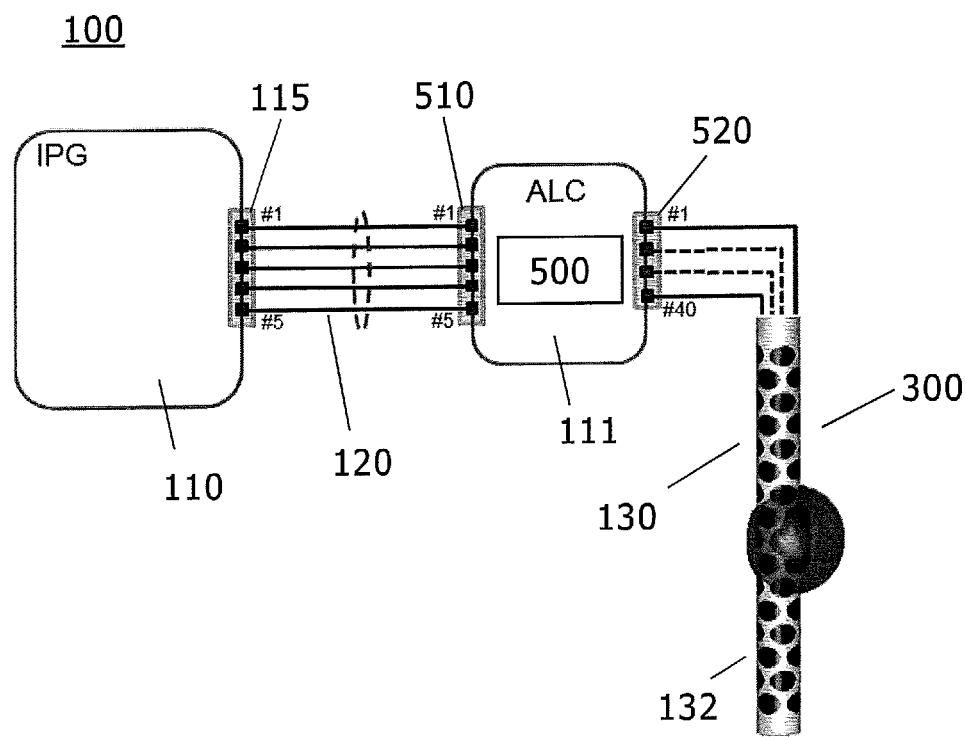
FIG. 4: a schematical drawing of a probe system according to the present invention with an electronic module.
Figure 7:
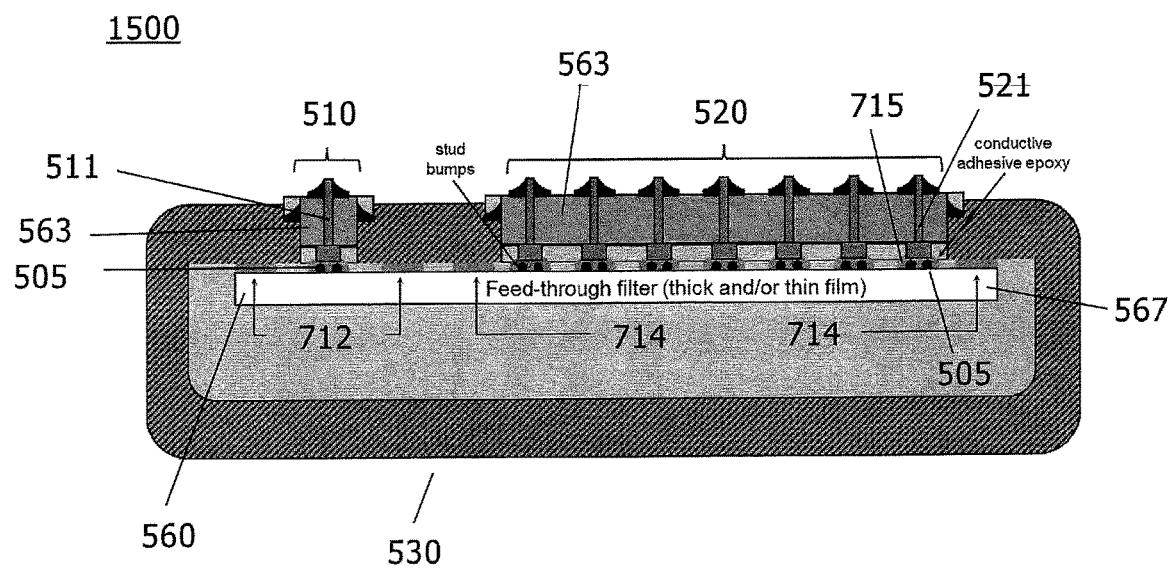
FIG. 7: a schematical cross-sectional view of the electronic module according to a second embodiment.
Figure 8:
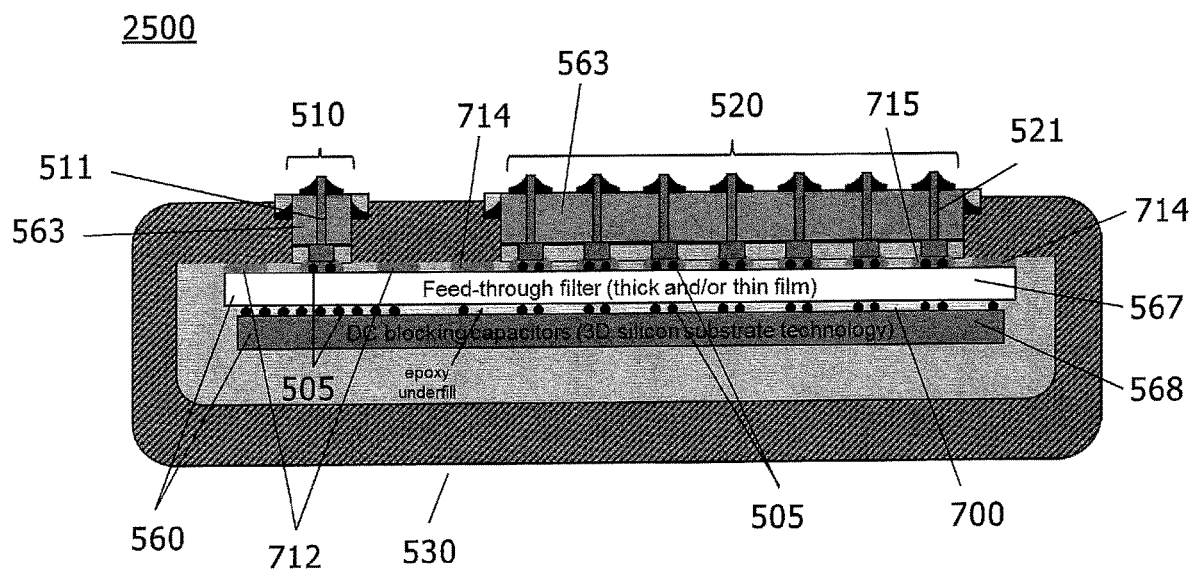
FIG. 8: a schematical cross-sectional view of the electronic module according to a third embodiment.
Figure 9:
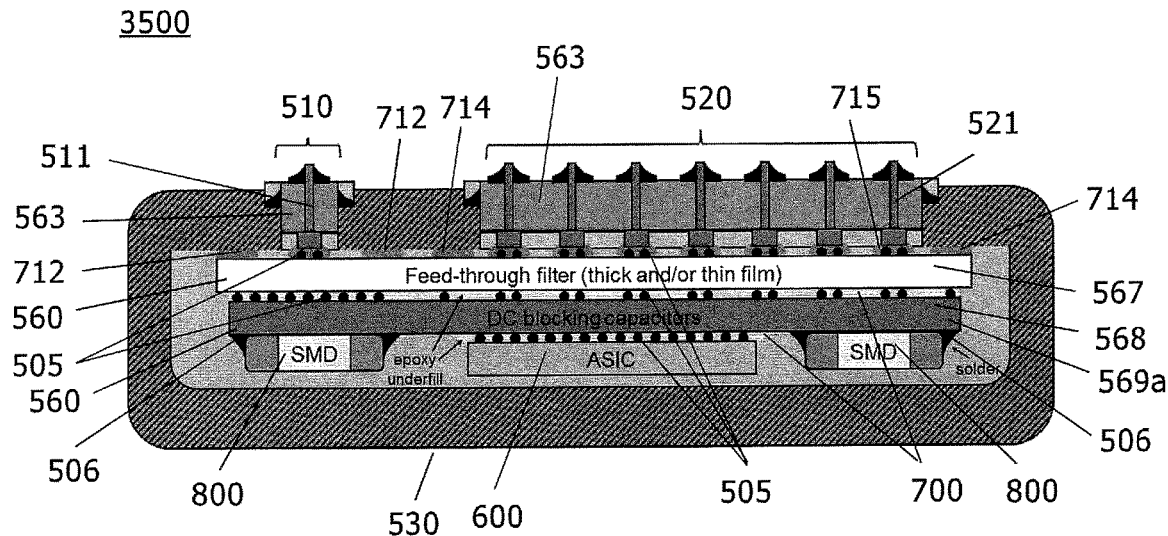
FIG. 9: a schematical cross-sectional view of the electronic module according to a fourth embodiment.

FIG. 4 shows a schematical drawing of a system 100 for brain applications according to the present invention with an electronic module 500. The electronic module 500 (which can be also an electronic module 1500, 2500, 3500 as shown in FIGS. 7 to 9) is in this embodiment integrated into the active lead can 111.

As can be seen in the embodiments shown in FIGS. 6 to 9 of the possible embodiments of the electronic module 500, 1500, 2500, 3500, the electronic module 500, 1500, 2500, 3500 can comprise at least one integrated passive device 560. However, some aspects and embodiments of the invention are also advantageous independently from the use of an integrated passive device.

The system 100 having a DBS probe 130 as defined above comprises an IPG 110 and an active lead can 111 with an array of electronic switches that connects electrodes 132 arranged at the distal end of the lead 300 with the pulse generator lines of the implantable pulse generator 110. In addition, it includes neural recording facilities. IPG 110 and active lead can 111 are connected through an interface cable 120 with, here for example, five lines. Accordingly, the implantable pulse generator 110 has a 5-pin LCFX connector 115 which is connected via the interface cable 120 with the 5-pin LCFX connector 510 of the active lead can 111.

The active lead can 111 comprises a multi-pin connector with a 5-pin LCFX connector 510 for the interface cable 120 and a 40-pin HCFX connector 520 for the lead 300. It is mechanically possible to design these two feed-through connectors 510, 520 with a high pin density to reduce the area of the active lead can 111 significantly. However, this area advantage can only materialize if the electrical components of the active lead can 111 can be shrunk in similar proportions as the feed-through connectors 510, 520. Moreover, a very thin active lead can 111, most desirable to reduce its impact on skin erosion, not only requires a high pin density but also a reduction in the height of both feedthrough pins 511, 521 and interior electrical components. Thus both the electronics volume and area of the active lead can 111 are miniaturized to realize a small active lead can 111.

Note that techniques to shrink the active lead can 111 can also advantageously be applied to the implantable pulse generator 110, or any other implant module, for example, to trade for an increase in battery life time and/or increased functionality.

Figure 5:
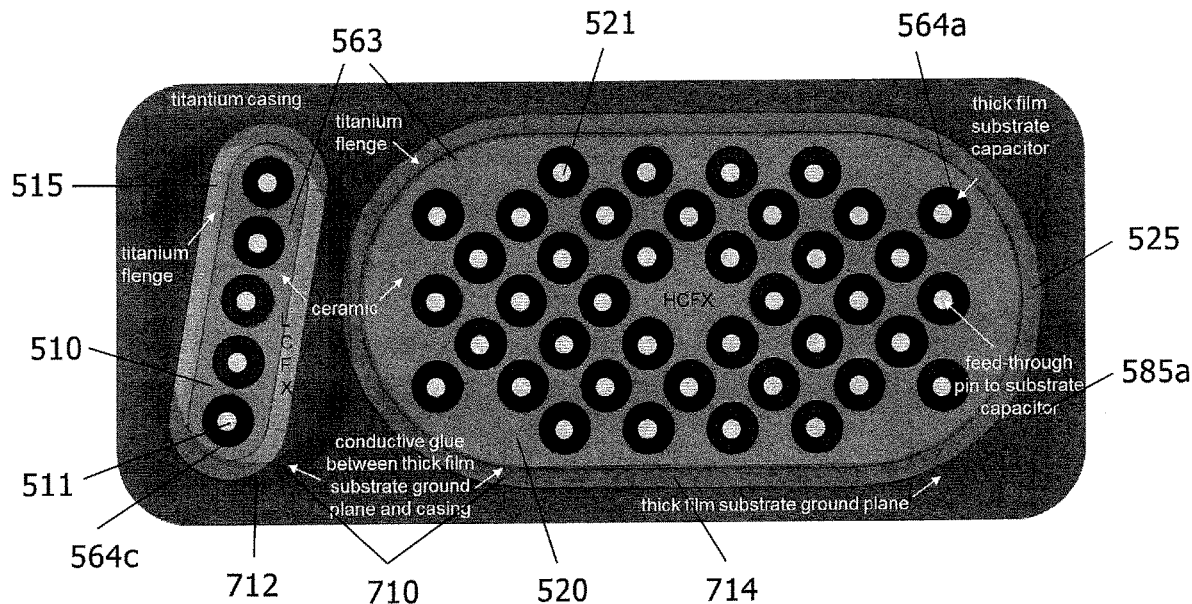
FIG. 5: a schematical top X-ray view of the electronic module showing the top feedthrough and the underlying feedthrough capacitor of the integrated passive device.

FIG. 5 shows an X-ray picture of the electronic module 500. In particular, FIG. 5 shows the top feedthrough and the underlying feed through capacitor of the integrated passive device. The embodiments of the electronic module 1500, 2500, 3500 shown in FIGS. 7 to 9 may be embodied similarly.

In FIG. 5, both the LCFX connector 510 and the HCFX connector 520 on the outside as well as the top of the substrate 568 (see e.g. FIG. 10) of the capacitor array on the inside, underneath the feedthrough, are shown. The ground plane 585 (see FIG. 10) of the capacitor array is electrically connected via the top part 585a of the ground plane to the housing 530 of the active lead can element 111 via a ring of conductive epoxy glue 710.

In particular, a ground ring of the LCFX connector 510 can be directly and/or indirectly electrically (galvanically, ohmically) connected to the housing 530 of the active lead can 111 via a ring of conductive epoxy glue 712 and/or a ground ring of the HCFX connector 520 can be directly and/or indirectly electrically (galvanically, ohmically) connected to the housing 530 of the active lead can 111 via a ring of conductive epoxy glue 714. It is also possible to apply a single ring of conductive epoxy glue surrounding both LCFX and HCFX connectors to electrically connect the housing 530 to the top ground plane 585a. If required, the feed through pins can be grouped into other combinations, in multiple sections or combined into just one single feed through.

The electronic module 500 (likewise the electronic modules 1500, 2500, 3500 of FIGS. 7 to 9) comprises HCFX connection pins 521 and LCFX connection pins 511. The HCFX connection pins 521 are connected to the DC blocking capacitors 564 of integrated passive device 568 (see e.g. FIGS. 12 and 13) and also to the feed-through filter capacitors 564a of integrated passive device 560 (see e.g. FIGS. 6 to 12). Although not explicitly shown, the LCFX connection pins 511 are also connected to integrated passive device 568 and integrated passive device 560 to realize the same DC blocking and EMI filtering for the LCFX.

Each feed-through pin 511, 521 contacts to a capacitor top contact 507 (see FIG. 10), which can be a gold top contact, on the substrate top of thick film integrated passive device 567. The HCFX pins 521 are contacted to capacitors 564a and the LCFX pins 511 are contacted to capacitors 564c. The top contacts 507 are simultaneously the top plates of capacitors 564a and capacitors 564c (see FIG. 10). Thus a thick film substrate with screen printed capacitors 564a and capacitors 564c forms a (single) feed-through filter substrate 567 (see e.g. FIGS. 6 to 12) that is directly put on top of and connected with the feedthrough pins 511, 521.

The LCFX connector 510 has a titanium flange 515 forming a border of the LCFX connector 510 and the HCFX connector 520 has a titanium flange 525 forming a border of the HCFX connector 520. The titanium flanges are integrated in the titanium active lead can housing 530.

Figure 6:
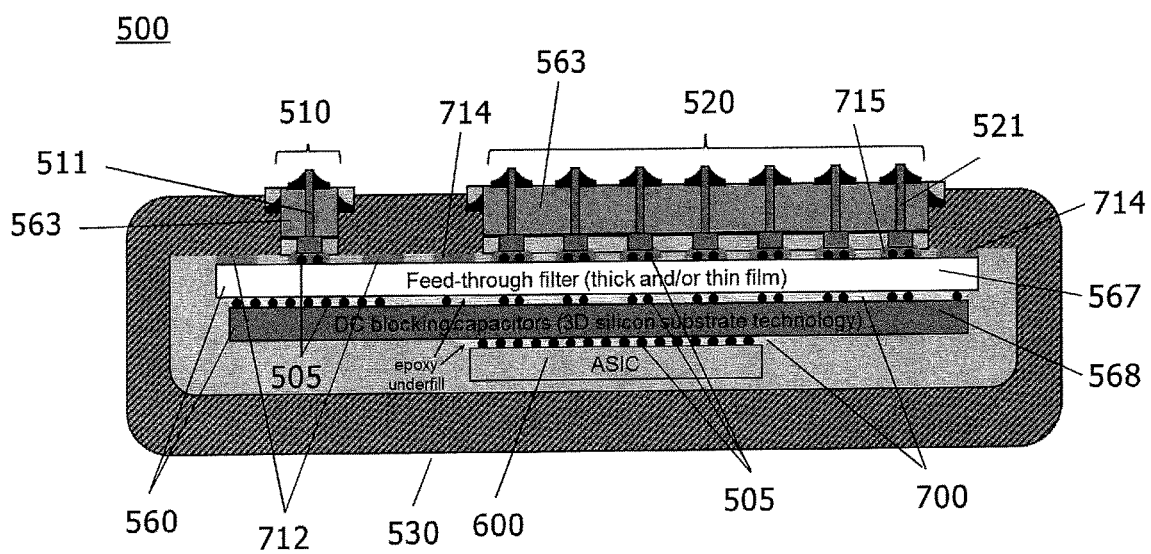
FIG. 6: a schematical cross-sectional view of the electronic module according to a first embodiment.

FIG. 6 shows a schematical cross-sectional view of the electronic module 500 according to a first embodiment and as shown in FIGS. 4 and 5.

The electronic module 500 comprises a filtering element, wherein the filtering element is a feed-through filter 567, and a blocking element, wherein the blocking element is a DC blocking element 564 and an ASIC 600, wherein especially the integrated passive device comprises the at least one filtering element, wherein the filtering element is exemplarily a feed-through filter, and/or the at least one blocking element, wherein the blocking element is exemplarily a DC blocking element.

The filtering can be provided by any means which is/are capable to provide a filtering. In particular, a filtering can be provided by any passive means or passive network.

The filtering element may be configured such that interferences, in particular unwanted interferences e.g. caused by mobile phones or the like, can be removed before the may enter e.g. a part of the housing for the electronics of the system for neural applications 100. Thereby, the advantage is achieved that a protection of the interior electronics against electromagnetic interference (EMI) is provided, for example, against mobile phone induced fields while the patient is using its mobile phone. The other way around, (high-frequency) interference generated inside the active lead can 111 is prevented to radiate outside.

The filtering element may be or may comprise e.g. an RF feed-through filter 567. The filter may comprise e.g. a capacitor, a coil, an inductor, a resistor or any other suitable passive component.

The blocking element may be configured such that in the event of a leakage current such leakage current, in particular DC leakage current flow is prevented. Regulations demand that (almost) no DC current flows through the patient carrying an implant such as a deep brain stimulator, even when a (single) failure occurs of, for example, the implant's electronics. This DC leakage design problem is solved by the application of DC blocking capacitors 564. Again, with a high number of feed-through pins 511, 522, it becomes mandatory to integrate those blocking capacitors 564 to achieve a minimum volume and area claim as opposed to the application of discrete components.

The ASIC 600 may comprise a part or e.g. all active electronics with some external passives, for example, power supply decoupling capacitors 800.

A substrate with integrated passives, here the integrated passive device 560, with e.g. resistors 570, capacitors 564a, 564b and 564c and inductors 575 (see e.g. FIGS. 11 and 12) may be used as substrate for off-chip (rerouting to) an ASIC 600. By the use of one or more application specific integrated circuits 600 the active electronic components of at least a part of the system for neural application 100 may be miniaturized.

Both for the novel feed-through filter 567 and the 3D silicon DC blocking capacitor technology a substrate is used for their realization, which opens up another unique opportunity to combine all electrical and electronics components into a single stack mounted on top of the feed-through pins 511 of the LCFX connector 510 and the feed-through pins 521 of the HCFX connector 520 directly as shown in FIG. 6. This 3-layer stack with the ASIC 600 on the DC blocking element 564 achieves a very high integration density.

Electrical connections are provided via stud bumps 505, which are embedded into epoxy underfill 700.

All active components of the implantable electronic device 111 (e.g., the ASIC 600) and passive (e.g. feed-through filters 567 and DC blocking capacitors 564) components of the active lead can 111 can be combined into a single stack and the stack can be mounted directly on top of the pins 521 of the HCFX connector 520 and the 5-pin 511 LCFX connector 510 (drawing is not true to scale).

FIG. 7 shows a further embodiment of the electronic module 1500, which is almost identical with the embodiment shown in FIG. 6 but without the DC blocking element 564 and the ASIC 600. All other features are identical and denoted with the same reference numbers.

FIG. 8 shows a further embodiment of the electronic module 2500, which is almost identical with the embodiment shown in FIG. 6 but without the ASIC 600. All other features are identical and denoted with the same reference numbers.

FIG. 8 shows a cross-section of the active lead can 111 interior with all DC blocking capacitors integrated onto a single integrated passive device 568 connected with stud bumps 505 to the (thick film) feed-through filter (array) 567. There is a lot of freedom for signal routing, because thick film interconnect layers can be realized on the (alumina)

substrate and/or integrated on the integrated passive device 560 substrate. Thus it is also possible to apply bond wiring instead of stud bumps to connect the feed-through filters with the DC blocking capacitors, because all connections can be routed to bond pads placed on the edges of both the filter substrate 560 bottom and DC blocking capacitor array substrate 568 top.

Figure 13:
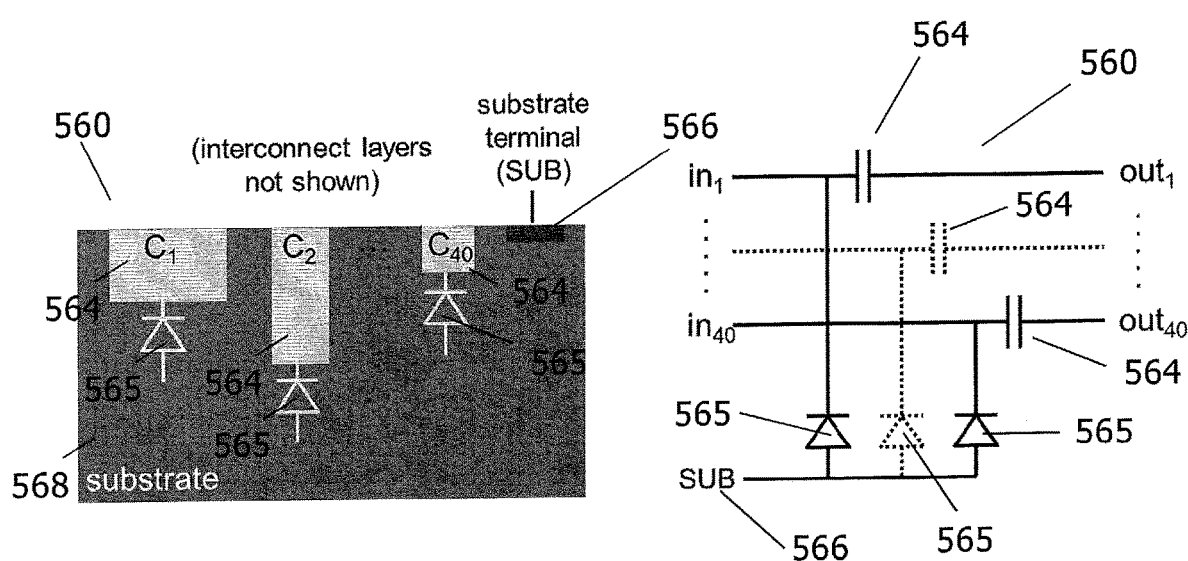
FIG. 13: a schematic drawing of a cross-section of an integrated passive device with multiple (floating) junction isolated (trench) DC blocking capacitors in a common substrate (left) with equivalent electrical circuit (right).

FIG. 13 shows the cross-section of a silicon based integrated passive device 560 that integrates all DC blocking capacitors 564 on a single die. Each capacitor 564 is a 3D trench capacitor realized in the substrate 568 itself (left picture). The capacitors are junction isolated and all diodes 565 share the common substrate 568 (right picture), and therefore, the substrate may need to be biased at an appropriate voltage so that all diodes 565 remain reversed biased during stimulation and recording.

Note that the (back-end) interconnect layers to signal and substrate bias pads are not shown in FIG. 13.

The integrated passive device 3D trench capacitors 564 match very well, their leakage performance is very good as well as their reliability and stability. Other passives can also be realized with this type of integrated passive device, although not always on the same substrate, for example, Transient Voltage Suppression (TVS) diodes to handle ESD, metal-insulator-metal (MIM) capacitors, resistors, integrated inductors, etc.

In the future, it might be possible to print feed-through capacitors 567 on the back side of a silicon integrated passive device substrate connected via substrate vias to the trench DC blocking capacitors on the other side. This would reduce the stack to a single, even thinner, integrated integrated passive device containing both the feed-through capacitors 567 as well as the DC blocking capacitors 564.

The fact that the active lead can 111 contains active electronics automatically leads to the need for an array of DC blocking capacitors 564 to prevent any potential DC current flow through the body and the feed-through filter 567 array as barrier for interferers (EMI).

FIG. 9 shows a further embodiment of the electronic module 2500, which is almost identical with the embodiment shown in FIG. 6 but with discrete surface mounted devices 800 (SMDs 800) mounted onto the DC blocking element 564. All other features are identical and denoted with the same reference numbers.

FIG. 9 shows that all circuitry can be combined in a single 3-layer stack with the ASIC 600 on top. This 3-layer stack forms an advanced hybrid with a very high integration density having a minimum volume and area claim.

If not all passive components are integrated in one or more integrated passive devices, the bottom of the silicon substrate 568 can be used as a (routing) substrate 569a for these components, for example realized by the shown discrete surface mounted devices (SMDs) 800. For example discrete DC blocking capacitors 564 that are too large to efficiently integrate in silicon, can be soldered with solders 506 on the bottom side of the silicon integrated passive device substrate 568 together with the ASIC 600.

Note that one could also resort to wire bonding instead of stud bumping to electrically connect the different layers of the active and passive stack of the active lead can 111.

The state-of-the-art feed-through capacitors that are integrated with the feedthrough pins themselves and that are today's industry's standard cannot be used for the high pin count of the active lead can 111 because:

1. their pin pitch is too large to match the pin density of an active lead can 111 and it is not possible to take full advantage of the mechanically achievable miniaturization of the feed-through connectors;
2. even more importantly, the application of these state-of-the-art feedthrough capacitors makes the active lead can 111 too thick;
3. and they are also not readily available in relatively low capacitance values which lead to unacceptable interface power consumption.

Figure 10:
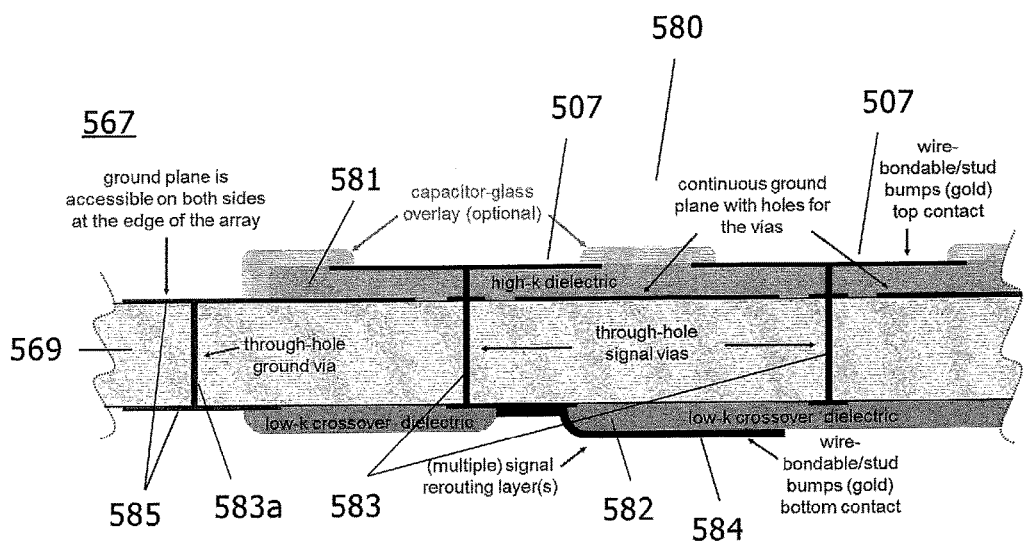
FIG. 10: a schematical cross-sectional view of a feedthrough capacitor in thick film technology.

A cross-section of (part of a) feed-through capacitor 567 array that does meet the stringent active lead can volume and area requirements is shown in FIG. 10. It can be realized with thin and/or thick film technology and/or with organic capacitors integrated into a flex foil or PCB. If realized in a thick film technology, an (alumina) substrate is used as carrier for the thick film layers printed on both sides of the substrate.

The feed-through capacitors 564a, 564c are (screen) printed on the top side of the substrate 568. The capacitors 564a, 564b and 564c are made of a sandwich of two (or more) conductive layers with a (relatively) high-k dielectric 581 in between. The printed top metal layer, preferably gold, provides the contacts 507 that are wire-bondable or appropriate for stud bumping so that stud bumps 505 and a conductive adhesive epoxy 715 can be used to reliably electrically connect the capacitor array to the feed-through pins 511, 521 of both LCFX and HCFX connector as shown in FIGS. 6 to 9. At the bottom of the substrate, one or more low-k crossover dielectric sections 582 may be provided.

FIG. 10 shows a cross-section of the feed-through filter 567 with a feedthrough capacitor array 580, containing capacitors 564a, 564b and 564c, in thick film technology. Each of the feed-through pins 511, 521 connects to a single capacitor in the array via stud bumps 505 on its (gold) top contact 507. Through-hole signal vias 583 connect the feed-through pins 511, 521 to one or more interconnect layers 584 on the bottom side of the substrate 568.

There are two important design aspects of the feed-through capacitor array 580 that must be met to guarantee the filter's interference suppression efficacy:

1. Each metal layer should have a maximum area fill factor so that a maximum overlap between all metal layers is achieved, increasing the capacitance per printed dielectric layer, and forming a (high-frequency) closed Faraday cage with the (titanium) housing 530 of the active lead can 111.

Thus a minimum spacing between the individual top contacts 507, and therefore a minimum spacing between the through-hole vias 583 and the ground plane 585 increase the filter's efficacy shown in FIG. 10, because it increases the capacitance per pin and more importantly, it minimizes the openings in the metal layers. Note that if desired, an additional ground plane 585 can be applied to electrically close the filter's 3D structure further.

2. The mutual ground plane 585 of all array capacitors extends beyond the capacitor array 580 of the LCFX connector 510 and HCFX connector 520 itself and is connected with a ring of ground vias 583a to the opposite side of the substrate to provide ground to the interior of the active lead can 111. Alternatively or additionally, the top and bottom substrate ground planes 585 can be connected via metallization wrapped around the ceramic substrate's 569 side edges.

The ground plane 585a on the substrate top is electrically connected to the housing 530 of the active lead can 111 via a ring of conductive adhesive epoxy 710 as shown in the top view in FIG. 5 and individually by the conductive epoxy (ring) 712 for the LCFX and the conductive epoxy (ring) 714 for the HCFX in FIGS. 6 to 9, so that the feed-through capacitor array 580 and the housing 530 together form a (high-frequency) closed, miniaturized Faraday cage only penetrated by the through-hole substrate vias 585, 583 (being connected with the feed-through pins 511, 521) from which interference signals (EMI) are diverted through feed-through capacitors 564a, 564b and 564c to the (titanium) housing before they can enter the housing itself.

Note that in FIG. 10, potentially, the capacitors in the array 580 can be designed with multiple ground-dielectric-signal layers to increase the capacitance/pin and/or enhance the efficacy of the (high-frequency) Faraday cage formed by housing 530 of the active lead can 111 and feed-through capacitor array 567.

Figure 11:
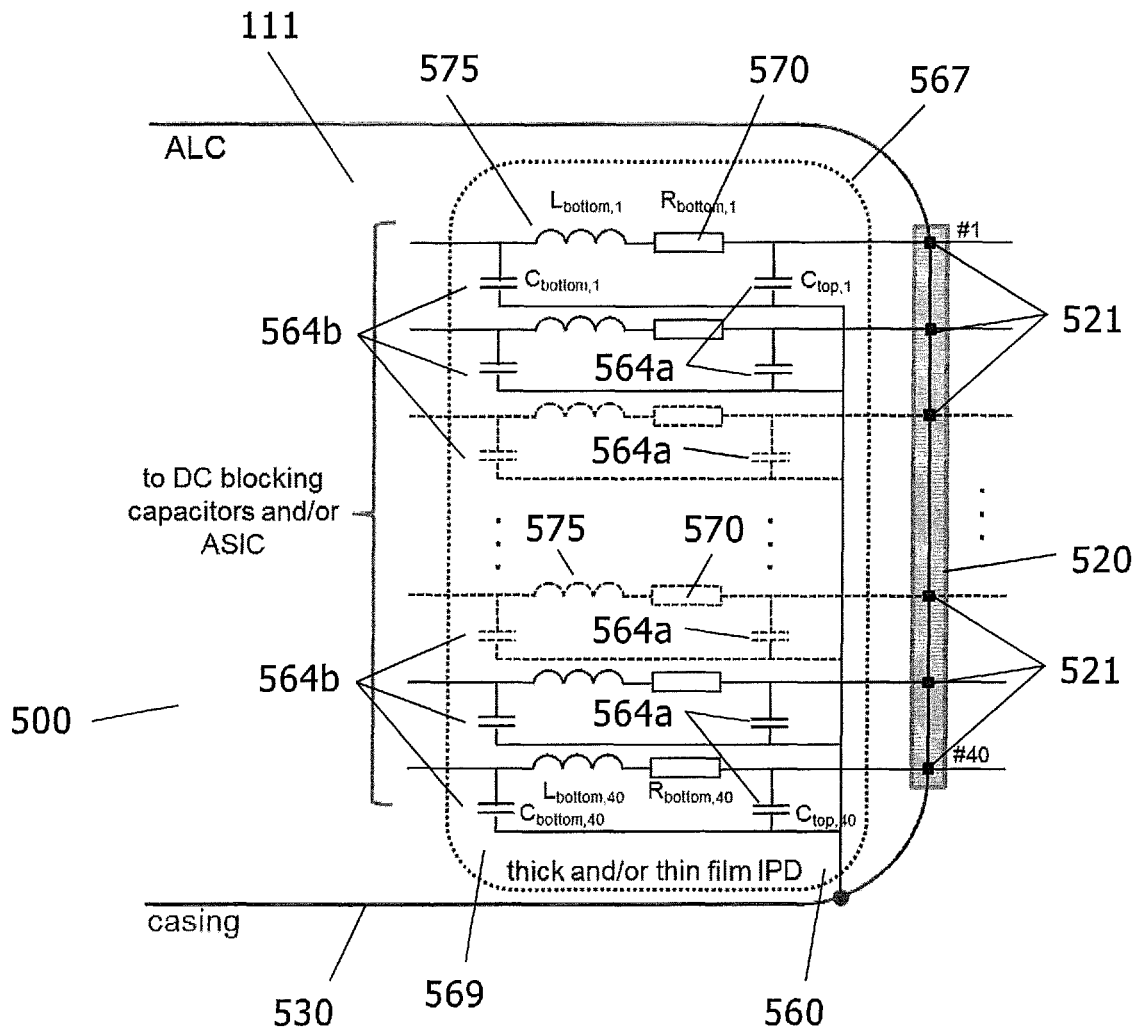
FIG. 11: a schematical view of the electronic module within an active lead can.

The capacitor array 580 on the substrate top can be part of a feed-through filter 567 extended with components printed on the substrate bottom as schematically shown in FIG. 11. A series resistor ($R_{bottom}$) 570 and/or inductor ($L_{bottom}$) 575 can be added to dampen any (parasitic) filter resonances and/or to increase the (series) impedance of the feed-through filter towards the electronics it is connected to. By this, the (high-frequency) shorting efficacy of the top capacitors ($C_{top}$) 564a of the feed-through filter to the housing may be improved. Preferably, another array of capacitors ($C_{bottom}$) 564b is printed on the substrate bottom to divert any remaining interference current to the housing.

Figure 12:
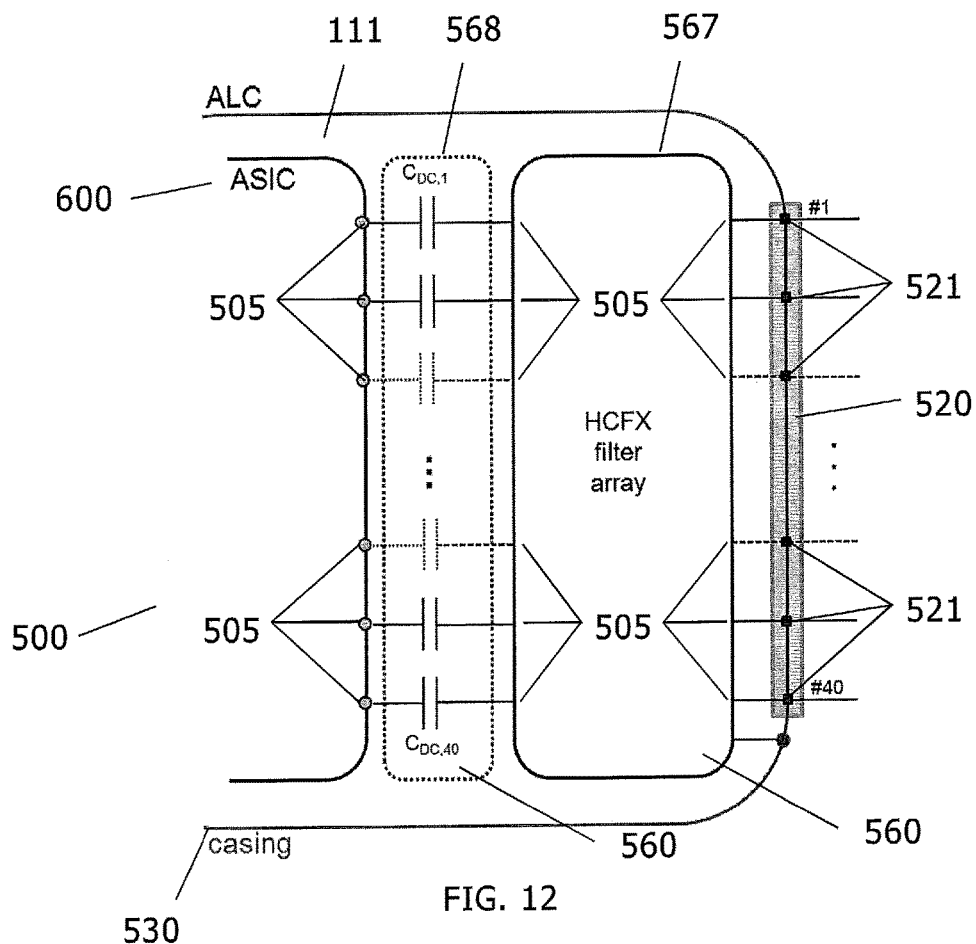
FIG. 12: a further schematical view of the electronic module within an active lead can as shown in FIG. 11.

As shown in FIGS. 11 and 12, the integrated passive device 560 may comprise series resistors 570, series inductors 575 and/or parallel capacitors 564b, wherein the resistors 570, the inductors 575 and/or the capacitors 564b are configured such that a (parasitic) filter resonance may be dampened and/or the filter's suppression, especially the suppression of electromagnetic interference, may be improved and/or increased.

For example, the series resistor 570, the inductor 575 and/or the parallel capacitor 564b can be added to dampen any (parasitic) filter resonances and/or to increase the filter's suppression, especially the suppression of electromagnetic interference. By this, the (high-frequency) shorting efficacy of the filter to the housing 530 may be improved.

The embodiment shown in FIGS. 11 and 12 relates to the embodiments shown in FIGS. 4 to 6, but could be also realized in total with the structure of the embodiment of the electronic module 3500 shown in FIG. 9 or similarly with the structure of the embodiments of the electronic module 1500, 2500 shown in FIGS. 7 and 8.

In particular, FIG. 11 shows a feed-through filter 567 with the top substrate capacitor array ($C_{top}$) extended with series inductor ($L_{bottom}$) 575, series resistor ($R_{bottom}$) 570 and another capacitor array ($C_{bottom}$) 564b printed on the substrate 568 bottom (HCFX connector 520 shown only).

If desired, another capacitor array ($C_{bottom}$) can be realized on the substrate bottom to suppress any remaining interference. This can be realized with thick or thin film technology on a ceramic substrate with vias, or one could resort to LTCC technology to realize the feed-through filter 567. LTCC stacks layers to form a substrate. The substrate is build out of green tape, where for each filter component (resistor 570, capacitors 564a, 564b, 564c and inductor 575) the most suitable green tape can be selected.

Note that although FIG. 11 shows the HCFX connections 520 only, a similar filter (strategy) can be applied at the LCFX connector 510 of both the active lead can 111 and the implantable pulse generator 110.

FIG. 12 shows an array of DC blocking capacitors 564 ($C_{DC}$) in-between ASIC 600 and HCFX filter array 567.

Regulations demand that (almost) no DC current flows through the patient carrying an implant such as a deep brain stimulator, even when a (single) failure occurs of, for example, the implant's electronics. This DC leakage design problem is solved by inserting DC blocking capacitors 564 (CDC) in series with all the implant's feed-through pins and/or feed-through filters as shown schematically for the HCFX connector 520 in FIG. 12.

The blocking capacitors 564 are also applied on the LCFX side, although not shown in FIG. 12, with a (potential) exception of the interface ground line between active lead can 111 and implantable pulse generator 110 which can directly be connected to the ASIC 600 and housing 530 being the housing of active lead can 111. The housing 530 is a conductive casing 530, preferably a titanium casing 530.

The volume and area claim of the DC blocking capacitors 564 become dominant again if an implant (module) such as the active lead can 111 has a high number of feed-through pins 511, 521. Even worse, the application of discrete capacitors, for example discrete surface mounted SMDs 800 (multi-layer ceramic capacitors (MLCCs); see FIG. 9), leads to a prohibitively large active lead can 111 enclosure with complex PCB interconnect.

FIG. 13 (left side) shows the cross-section of a typical silicon substrate based integrated passive device 560 with multiple junction isolated passive components (C1, C2, . . . ) in a common substrate 568 having a substrate terminal 566. Each component is junction isolated from the common integrated passive device 560 substrate 568. The back-end interconnect layers and detailed view of each component has been omitted.

As can be further seen in FIG. 13 (right side), the integrated passive device 560 with multiple junction isolated passive components (C1, C2, . . . ) may e.g. comprise capacitors 564 and diodes 565 as passive electronic components.

FIG. 13 (right side) shows an example of the equivalent electrical circuit of an integrated passive device 560 where each component (C1, C2, . . . ) is an integrated capacitor 564. The integrated passive device 560 has N input terminals (in1, . . . , inN) and N output terminals (out1, . . . , outN) and a single substrate terminal 566 that connects to all component-substrate junctions simultaneously. Resistance as part of interconnect, components and substrate has been left out of the equivalent circuit for simplicity. So, FIG. 13 (right side) shows an integrated passive device 560 equivalent electrical circuit for an integrated capacitor array wherein the single substrate terminal 566 is connected to all component substrate diodes 565 simultaneously.

This above aspects and embodiments of the invention can advantageously be used in all active implantable medical devices that contain active electronics with connections to the body, where the mechanical miniaturization is hampered by the volume and/or area claim of the passive electrical components and networks, in particular, when the active implantable medical device has a high feed-through pin density.

By the embodiments and aspects of the invention an electronic module for a system for neural applications is provided that comprises a housing and a filtering element that together form a (high-frequency) closed, miniaturized Faraday cage.

The housing is made of an electrically conductive material, as for example titanium. According to this aspect of the invention, the Faraday cage is formed by a combination of the housing and the filtering element.

Advantageously, the filtering element forms an integral part of the housing. The filtering element can be configured as a feed-through filter.

The filtering element can be configured as an electromagnetic interference (EMI) filter, in particular as EMI feed-through filter. In this regard, the filtering element can comprise filter capacitors, in particular feed-through capacitors. The housing has at least one portion which is not entirely or sufficiently closed by conductive material, i.e. the housing has at least one portion comprising at least partially material that is not electrically conductive. The at least one portion of the housing comprising non-conductive material can be due to feed-through pins. The feed through pins can be capacitively coupled to the housing. The Faraday cage is closed by the filtering element with respect to the at least one portion of the housing comprising non-conductive material. In particular, the filtering element can comprise a substrate that is configured to close the Faraday cage with respect to the at least one portion of the housing comprising non-conductive material. The filtering element can comprise at least one electrically conductive layer, in particular at least one electrically conductive plane or plate that is configured to close the Faraday cage with respect to the non-conductive area of the housing. The filtering element is therefore advantageously arranged in and close to the area (portion) where the housing is insufficiently closed by conductive material. The capacitors can be coupled with one side to the electrically conductive layer. The conductive layer can be a ground plate/plane of the substrate, in particular a common ground plane of the capacitors.

The ground plate/plane may be have a different potential as the electronics module system ground (GND), i.e. the ground plate/plane can be connected to system ground (GND), but this is not mandatory for the Faraday cage to function properly.

The conductive layer can then be galvanically coupled to the conductive housing. Advantageously, the conductive layer (substrate) is designed to cover most of the at least one area or portion where the housing is insufficiently closed in terms of a Faraday cage. The substrate and conductive layer are advantageously only interrupted by very small holes or areas for vias leading/penetrating through the substrate. A plate of the capacitors (564a, 564c) can then advantageously be arranged such that it at least partially overlaps an area without conductive layer (585) due to the vias (this can be seen in FIG. 10 where layer 507 overlaps the areas free of layer 585 due to vias 583. This configuration basically closes the gaps in the conductive layer 585 due to vias. So, the Faraday cage is formed by the housing itself and the conductive continuous ground plane 585 in FIG. 10 that is glued to the housing. The continuous ground plane 585 has holes in it for the through-hole signal vias 583, as signals have to be brought to the inside of the electronic module (ALC). Thus, these holes form openings in the otherwise electrically closed Faraday cage. In order to prevent EMI currents from entering the inside of the electronic module via these signal vias, capacitors are connected between each incoming feed-through pin 511, 521 and the housing 530 (via the ground plane 585 glued to the housing) to divert EMI currents to the housing. In this way, the Faraday cage is electrically closed again (by plates 507 in FIG. 10 which also serve as connecting stud bumps for the feed-through pins 511, 521) despite the openings in the ground plane 585 and the through-hole signal vias to the inside of the ALC. The feed-through pins 511, 521 themselves are held together by the non-conductive ceramic 563 (see FIG. 9). This non-conductive ceramic 563 leads to openings in the (titanium) housing 530 for EMI and is referred to as the non-conductive material. The large opening for EMI is formed by the non-conductive material 563. The ground plane 585 (also referred to as first conductive layer or main conductive layer) on the substrate top can form the common bottom plate of all FX capacitors.

Alternatively, the FX pins may be made in a completely conducting housing but there may be a small insulation between pins and housing. In that case, also well-working Faraday cage is formed. There would be still the need for filtering EMI, but there are no pins in a common ceramic anymore.

In other words, this aspect of the invention benefits from the realization of a thin EMI filter on or in a substrate. The filter can advantageously be manufactured in thin and/or thick film technology. The application and design of this substrate form a miniaturized Faraday cage (i) by the way the EMI filter is constructed, namely a ground plane that extends to the substrate's edges and penetrated by small holes for the signal vias only, (ii) by galvanically connecting this substrate or more specifically its ground plane to the housing with conductive material, like for example conductive epoxy, and (iii) by preventing signals to enter the inside of the electronic module through the signal vias by diverting any EMI currents via the EMI filter capacitors to the housing.

This means that the Faraday cage can be formed by the housing and the chosen design of the filter capacitors (for example FX filter capacitors). More specifically the Faraday cage can be formed by the ground plate that all capacitors have in common and which is glued to the conductive titanium housing.

According to aspects of the invention, a filter (filtering element) is applied, preferably as an integral part of the Faraday cage, to divert the high-frequency EMI to the housing i.e. outside of the Faraday cage while passing the intended low(er)-frequency signals to the electronics inside of it.

Furthermore, the electronic module can comprise a substrate and the substrate can comprise a contact surface portion, which is connected to the housing of the electronic module, so that the feed-through capacitors and the housing together form the (high-frequency) closed, miniaturized Faraday cage.

The contact surface portion can be connected to the housing electrically and/or capacitively. The contact surface portion can be a ground plane on the substrate top. The contact surface portion can be connected to the housing via a ring of conductive adhesive. The conductive adhesives can be conductive adhesive epoxy. All these aspects advantageously contribute to less vulnerability to EMI.

The substrate can comprise holes, wherein through-hole signal vias can connect the feed-through pins to one or more interconnect layers on the bottom side of the substrate.

The electronic module configured as a Faraday-cage can comprises at least one filtering element as previously described. The electronic module can further comprise at least one blocking element. The filtering element can be a feed-through filter. The blocking element can be a DC blocking element.

The electronic module configured as a Faraday-cage can comprise several sections of interconnects such as one or more low-count feed-through pins and/or one or more high-count feed-through pins.

The electronic module configured as a Faraday cage can comprise an ASIC and/or another integrated passive device and/or at least one bias terminal.

The electronic module configured as a Faraday cage can be connected or connectable to several sections of interconnects such as one or more low-count feed-through pins and/or one or more high-count feed-through pins.

The electronic module configured as a Faraday cage can comprise at least one first connector element and at least one second connector element.

The first connector element can be configured such that the electronic module is connectable or connected to a controller which is at least configured to supply or provide at least one electrical signal.

The electronic module configured as a Faraday cage can comprise at least one first connector element and at least one second connector element, the first connector element being configured such that the electronic module is connectable or connected to a controller which is at least configured to measure at least one electrical signal. The second connector element can be configured such that the electronic module is connectable or connected to a lead for neural stimulation and/or recording. The second connector element can be configured such that the electronic module is connectable or connected to an active lead can element and/or to a housing. The electrical signal can include at least one voltage and/or at least one current and/or at least one voltage waveform and/or at least one current waveform. The controller can be configured to supply or provide the electrical signal via at least one output and/or to measure the electrical signal via at least one input. The output can be a stimulation and/or clock and/or power and/or communications output. The input can be a recording and/or power and/or clock and/or communications input.

The ASIC may amplify via a second connector element analog neural signal into digital data that are sent to a controller, e.g. an IPG. This can be done e.g. via a communication interface line.

With respect to the above described configuration of the Faraday cage, the first connector and/or the second connector and the respective feed-through pins of the connector form the portion(s) and or area(s) of the housing of the electronic module which are advantageously covered by the substrate, in particular the conductive layer of the substrate of the filtering element. The filtering element can then advantageously be arranged beneath the first connector and/or the second connector. An arrangement where the filtering element, in particular the substrate of the filtering element and more specifically the conductive layer of the substrate is overlaps (or extends over) the outer edge of the first and/or second connector in order to fully cover the area of the connector(s). This can also allow the contact surface portion of the filtering element to be galvanically coupled to the housing.

Furthermore, the filtering element, the substrate of the filtering element, and/or the conductive layer (or several conductive layers) of the filtering element are configured such the conductive areas (pads, stud bumps, gold contacts) coincide with interconnecting areas of feed-through pins of the first connector and/or second connector. This allows the filtering element to be placed and connected directly beneath the first connector and/or connector.

The substrate can be a ceramic substrate or a silicon substrate or flex foil or PCB.

The electronic module can comprise at least partially a multi-layer structure. The filtering element can then form a first layer. The blocking element can form a second layer. The application specific integrated circuit (ASIC) can forms a third layer.

The module can comprise a dedicated routing substrate and/or an already available substrate for routing for passive components.

The filtering element can comprise at least one passive component, however, typically there are more passive components arranged on or in the filtering element.

The passive component can be at least one discrete component such as a surface mounted device (SMD). The passive component can also be a thin or thick film element or an integrated component.

The passive component can be at least one out of a resistor and an inductor and a capacitor. The resistor and/or the inductor and/or capacitor can be configured such that a (parasitic) filter resonance may be dampened. The resistor and/or the inductor and/or capacitor can be configured such that the filter's suppression such as the suppression of electromagnetic interference may be improved or increased. The resistor can be a series resistor and/or the inductor can be a series inductor and/or the capacitor can be a parallel capacitor.

The invention also provides a lead for neural stimulation comprising at least one electronic module configured as a Faraday cage for a system for neural applications according to the previously mentioned aspects.

The electronic module configured as a Faraday cage can be configured as an implant or implantable device of any kind. Advantageously, the electronic module can also be an implantable pulse generator.

From the previously described embodiments, it can be seen that an electronic module 500, 1500, 2500, 3500 for a system for neural applications 100 is provided comprising a housing 530 and a filtering element 567 that form a (advantageously high-frequency) closed, miniaturized Faraday cage The housing 530 can be formed of an electrically conductive material, as for example titanium. According to this aspect of the invention, the Faraday cage is formed by a combination of the housing and the filtering element.

Advantageously, the filtering element 567 forms an integral part of the housing. The filtering element 567 can be configured as a feed-through filter. The filtering element can be configured as an electromagnetic interference (EMI) filter, in particular as EMI feed-through filter. In this regard, the filtering element can comprise filter capacitors 564a, 564c, in particular feed-through capacitors. The housing has at least one portion (see areas for connectors 510, 520) which is not entirely or sufficiently closed by conductive material, i.e. the housing has at least one portion comprising at least partially material that is not electrically conductive. The at least one portion of the housing comprising non-conductive material can be due to feed-through pins 511, 521. The Faraday cage is closed by the filter 567 with respect to the at least one portion of the housing comprising non-conductive material. In particular, the filtering element can comprise a substrate 569 that is configured to close the Faraday cage with respect to the at least one portion of the housing comprising non-conductive material 563 (for example non-conductive ceramic). The filtering element 567 can comprise an electrically conductive layer 585, in particular an electrically conductive plane or plate that is configured to close the Faraday cage with respect to the non-conductive area of the housing. In FIG. 7 (also in FIGS. 6, 8, 9 and 10) it can be seen that the filtering element is arranged in and close to (beneath) the area or portion (area of connectors 510, 520 and respective feed through-pins 511, 521) where the housing is insufficiently closed by conductive material. The capacitors 564a, 564c can be coupled with one side to the electrically conductive layer 585. The conductive layer 585 can be a ground plate/plane of the substrate, in particular a common ground plane of the capacitors. The conductive layer 585 can then be galvanically coupled to the conductive housing. Advantageously, the conductive layer 585 (substrate) is designed to cover most of the at least one area or portion where the housing is insufficiently closed in terms of a Faraday cage. The substrate 569 and/or the conductive layer 585 is/are only interrupted by very small holes or areas for vias 583 leading/penetrating through the substrate. However, these areas are covered by another conductive layer that is configured as a plate (507) of a feed-through capacitor 564a, 564c.

In other words, this aspect of the invention benefits from the realization of a thin EMI filter on a substrate. The filter can advantageously be manufactured in thin and/or thick film technology. The application and design of this substrate form a miniaturized Faraday cage (i) by the way the EMI filter is constructed, namely a ground plane that extends to the substrate's edges and penetrated by small holes for the signal vias only, (ii) by galvanically connecting this substrate or more specifically its ground plane to the housing with conductive material, like for example conductive epoxy, and (iii) by preventing signals to enter the inside of the electronic module through the signal vias by diverting any EMI currents via the EMI filter capacitors to the housing.

This means that the Faraday cage can be formed by the housing and the chosen design of the filter capacitors (for example FX filter capacitors). More specifically the Faraday cage can be formed by the ground plate that all capacitors have in common and which is glued to the conductive titanium housing.

According to aspects of the invention, a filter (filtering element) 567 is applied, preferably as an integral part of the Faraday cage, to divert the high-frequency EMI to the housing i.e. outside of the Faraday cage while passing the intended low(er)-frequency signals to the electronics inside of it.

Furthermore, the electronic module can comprise a substrate and the substrate can comprise a contact surface portion 585, which is connected to the housing 530 of the electronic module, so that the conductive layer 585 and the feed-through capacitors 564a, 564c and the housing together form the (high-frequency) closed, miniaturized Faraday cage.

The electronic module configured as a Faraday cage can comprise at least one first connector element 510 and at least one second connector element 520.

The first connector element 510 can be configured such that the electronic module is connectable or connected to a controller which is at least configured to supply or provide at least one electrical signal.

The electronic module configured as a Faraday cage can comprise at least one first connector element 510 and at least one second connector element 520, the first connector element 510 being configured such that the electronic module is connectable or connected to a controller which is at least configured to measure at least one electrical signal. The second connector element 520 can be configured such that the electronic module is connectable or connected to a lead for neural stimulation and/or recording. The second connector element 520 can be configured such that the electronic module is connectable or connected to an active lead can element and/or to a housing.

With respect to the above described configuration of the Faraday cage, the first connector 510 and/or the second connector 520 and the respective feed-through pins of the connector(s) 510, 520 form the portion(s) and or area(s) of the housing of the electronic module which are advantageously covered by the substrate 569, in particular the conductive layer 585 of the substrate of the filtering element. The filtering element 567 can then advantageously be arranged beneath the first connector 510 and/or the second connector 520. An arrangement where the filtering element, in particular the substrate 569 of the filtering element 567 and more specifically the conductive layer 585 of the substrate is overlaps (or extends over) the outer edge of the first and/or second connector in order to fully cover the area of the connector(s). This can also allow the contact surface portion of the filtering element to be galvanically coupled to the housing.

Furthermore, the filtering element 567, the substrate 569 of the filtering element, and/or the conductive layer 585 (or several conductive layers) of the filtering element are configured such the conductive areas 507 (pads, stud bumps, gold contacts) coincide with interconnecting elements of feed-through pins 511, 521 of the first connector and/or second connector. This allows the filtering element to be placed and connected directly beneath the first connector and/or second connector.

The contact surface portion 585 can be a ground plane on the substrate top. The contact surface portion 585 can be connected to the housing 530 via a ring of conductive adhesive. The conductive adhesive is a conductive adhesive epoxy 715, 712, 714. The substrate can comprise holes 583, wherein through-hole signal vias connect the feed-through pins 511, 521 to one or more interconnect layers on the bottom side of the substrate 569.

The electronic module 500, 1500, 2500, 3500 can be connectable or connected to a lead 300 for neural stimulation and/or recording. The second connector element 520 can be configured such that the electronic module 500 is connectable or connected to an active lead can element 111 and/or to the housing 530.

The electrical signal can include at least one voltage and/or at least one current and/or at least one voltage waveform and/or at least one current waveform.

The controller can be configured to supply or provide the electrical signal via at least one output and/or to measure the electrical signal via at least one input 521.

The output can be a stimulation and/or clock and/or power and/or communications output.

The input can be a recording and/or power and/or clock and/or communications input.

The electronic module 500, 1500, 2500, 3500 can comprises at least partially a multi-layer structure. The filtering element 567 can then form a first layer. The blocking element 568 can form a second layer. The application specific integrated circuit (ASIC) 600 can form a third layer. The electronic module can comprise a dedicated routing substrate and/or an already available substrate 569a for routing for passive components. The electronic module 500, 1500, 2500, 3500 can further comprise a passive component, wherein the passive component is at least one discrete component such as a surface mounted device (SMD) 800. The passive component can be at least one out of a resistor 570 and an inductor 575 and a capacitor 564a, 564b, 564c. The resistor 570 and/or the inductor 575 and/or capacitor 564a, 564b, 564c can be configured such that a parasitic filter resonance may be dampened. The resistor 570 and/or the inductor 575 and/or capacitor 564a, 564b, 564c can be configured such that the filter's suppression such as the suppression of electromagnetic interference may be improved or increased.

With respect to the Faraday cage, it should be noted again that the above mentioned design aspects of the feed-through capacitors should be met to guarantee the filter's interference suppression efficacy. These design requirements may also be achieved without necessarily using an integrated passive device. These design aspects guarantee the filter's interference suppression efficacy. Accordingly, each metal layer should have a maximum area fill factor so that a maximum overlap between all metal layers is achieved, increasing the capacitance per printed dielectric layer, and forming a (high-frequency) closed Faraday cage with the (titanium) housing 530 of the active lead can 111. A minimum spacing between the individual top contacts 507, and therefore a minimum spacing between the through-hole vias 583 and the ground plane 585 should be achieved (FIG. 10). If desired, an additional ground plane 585 can be applied to electrically close the filter's 3D structure further. The mutual ground plane 585 of all array capacitors extends beyond the capacitor array 580 of the LCFX connector 510 and HCFX connector 520 itself and can be is connected with a ring of ground vias 583a to the opposite side of the substrate to provide ground to the interior of the active lead can 111. In particular, it is sufficient that the mutual capacitor plane is galvanically connected to the housing to have a good EMI filter integrated in the Faraday cage.

Alternatively or additionally, the top and bottom substrate ground planes 585 can be connected via metallization wrapped around the ceramic substrate's 569 side edges.

In the aspects and embodiments of the invention, in particular with respect to the Faraday cage, the filtering element can be an integrated passive device.

The aspects and embodiments of the invention can be used in all active implantable medical devices that contain active electronics with connections to the body, where EMI is an issue.

Further items being explicitly disclosed herein are:
1. An electronic module (500) for a system for neural applications (100), wherein the electronic module (500) comprises at least one integrated passive device (560).
2. The electronic module (500) according to item 1, characterized in that
   the electronic module (500) comprises at least one filtering element and/or at least one blocking element.
3. The electronic module (500) according to item 2, characterized in that
   the filtering element is a feed-through filter (567).
4. The electronic module (500) according to item 2, characterized in that
   the blocking element is a DC blocking element (568) and/or at least one application specific integrated circuit (ASIC) (600).
5. The electronic module (500) according to one of items 2 to 4, characterized in that
   the integrated passive device (560) comprises the at least one filtering element and/or the at least one blocking element.
6. The electronic module (500) according to one of the preceding items, characterized in that
   the integrated passive device (560) comprises several sections of interconnects such as one or more low-count feed-through pins (511) and/or one or more high-count feed-through pins (521).
7. The electronic module (500) according to one of the preceding items, characterized in that
   the integrated passive device (560) comprises an ASIC (600) and/or another integrated passive device and/or at least one bias terminal.
8. The electronic module (500) according to one of the preceding items, characterized in that
   the integrated passive device (560) is connected or connectable to several sections of interconnects such as one or more low-count feed-through pins (511) and/or one or more high-count feed-through pins (521).
9. The electronic module (500) according to one of the preceding items, characterized in that
   the integrated passive device (560) is connected or connectable to an ASIC (600) and/or another integrated passive device and/or at least one bias terminal.
10. The electronic module (500) according to one of items 6 to 9, characterized in that
    an in- and/or output of the integrated passive device is connected to a filtered out- and/or input via at least one capacitor (564, 564a, 564b, 564c) and/or at least one resistor (570) and/or at least one inductor (575).
11. The electronic module (500) according to one of the preceding items, characterized in that
    the integrated passive device comprises a substrate (568) and at least one diode (565) and/or at least one passive electronic component which is/are arranged on and/or in the substrate.
12. The electronic module (500) according to one of the preceding items, characterized in that
    the electronic module (500) comprises at least one first connector element (510) and at least one second connector element (520), the first connector element (510) being configured such that the electronic module (500) is connectable or connected to a controller (110) which is at least configured to supply or provide at least one electrical signal.
13. The electronic module (500) according to one of the preceding items, characterized in that
    the electronic module (500) comprises at least one first connector element (510) and at least one second connector element (520), the first connector element (510) being configured such that the electronic module (500) is connectable or connected to a controller (110) which is at least configured to measure at least one electrical signal.
14. The electronic module (500) according to item 12 or 13, characterized in that
    the second connector element (520) is configured such that the electronic module (500) is connectable or connected to a lead (300) for neural stimulation and/or recording.
15. The electronic module (500) according to one of items 12 to 14, characterized in that
    the first connector element (510) and/or second connector element (520) is configured such that the electronic module (500) is connectable or connected to an active lead can element (111) and/or to a housing (530).

16. The electronic module (500) according to one of items 12 to 15,
characterized in that
the electrical signal includes at least one voltage and/or at least one current and/or at least one voltage waveform and/or at least one current waveform.

17. The electronic module (500) according to one of items 12 to 16,
characterized in that
the controller is configured to supply or provide the electrical signal via at least one output and/or to measure the electrical signal via at least one input (521).

18. The electronic module (500) according to item 17,
characterized in that
the output is a stimulation and/or clock and/or power and/or communications output.

19. The electronic module (500) according to item 17 or 18,
characterized in that
the input is a recording and/or power and/or clock and/or communications input.

20. The electronic module (500) according to one of the preceding items,
characterized in that
the integrated passive device (560) comprises one or more passive electronic components (564, 565, 566).

21. The electronic module (500) according to one of the preceding items,
characterized in that
the integrated passive device (560) comprises only one or more passive electronic components (564, 565, 566).

22. The electronic module (500) according to one of the preceding items,
characterized in that
the integrated passive device (560) comprises at least one capacitor (564) and/or at least one inductor and/or at least one diode (565) and/or at least one substrate terminal (566).

23. The electronic module (500) according to one of the preceding items,
characterized in that
the integrated passive device (560) comprises only capacitors and/or inductors and/or diodes and/or at least one substrate terminal (566).

24. The electronic module (500) according to one of the preceding items,
characterized in that
the integrated passive device (560) comprises one or more feed-through capacitors (564a, 564b, 564c) which are mounted on and/or integrated into a substrate (567).

25. The electronic module (500) according to one of the preceding items,
characterized in that
the integrated passive device (560) comprises one or more integrated DC blocking capacitors (564) which are mounted on or integrated into a substrate (568).

26. The electronic module (500) according to item 25,
characterized in that
the substrate is a ceramic substrate (569).

27. The electronic module (500) according to item 25,
characterized in that
the substrate is a silicon substrate (568).

28. The electronic module (500) according to one of items 6 to 27,
characterized in that
the substrate (569) comprises a contact surface portion (585), which is connected to a housing (530) of the electronic module (500), so that the feed-through capacitors (564a, 564b, 564c) and the housing (530) together form a (high-frequency) closed, miniaturized Faraday cage only penetrated by through-hole substrate vias (585, 583) that are capacitively and/or electrically coupled to the Faraday cage.

29. The electronic module (500) according to item 28,
characterized in that
the contact surface portion (585) is connected to the housing (530) galvanically and/or electrically and/or capacitively.

30. The electronic module (500) according to item 28 or 29,
characterized in that
the contact surface portion (585) is a ground plane (585) on the substrate top.

31. The electronic module (500) according to one of items 28 to 30,
characterized in that
the contact surface portion (585) is connected to the housing (530) via a ring of conductive adhesive.

32. The electronic module (500) according to item 31,
characterized in that
the conductive adhesive is a conductive adhesive epoxy (715, 712, 714).

33. The electronic module (500) according to one of items 30 to 32,
characterized in that
the ground plane (585) is only penetrated by through-hole substrate signal vias (585, 583).

34. The electronic module (500) according to one of items 28 to 32,
characterized in that
the substrate comprises holes (583), wherein through-hole signal vias connect the feed-through pins (511, 521) to one or more interconnect layers on the bottom side of the substrate (569).

35. The electronic module (500) according to one of the preceding items,
characterized in that
the electronic module (500) comprises at least partially a multi-layer structure.

36. The electronic module (500) according to item 35,
characterized in that
the filtering element (567) forms a first layer.

37. The electronic module (500) according to item 35 or 36,
characterized in that
the blocking element (568) forms a second layer.

38. The electronic module (500) according to one of items 35 to 37,
characterized in that
the application specific integrated circuit (ASIC) (600) forms a third layer.

39. The electronic module (500) according to one of the preceding items,
characterized in that
the module (500) comprises a dedicated routing substrate and/or an already available substrate for routing (569a) for passive components which are mounted outside an integrated passive device (560).

40. The electronic module (500) according to item 38,
characterized in that
the passive component is at least one discrete component such as a surface mounted device (SMD) (800).

41. The electronic module (500) according to one of the preceding items,
characterized in that
the integrated passive device (560) comprises at least one resistor (570) and/or an inductor (575) and/or a capacitor (564*a*, 564*b*, 564*c*).

42. The electronic module (500) according to item 41,
characterized in that
the resistor (570) and/or the inductor (575) and/or capacitor (564*a*, 564*b*, 564*c*) is/are configured such that a (parasitic) filter resonance may be dampened.

43. The electronic module (500) according to item 41 or 42,
characterized in that
the resistor (570) and/or the inductor (575) and/or capacitor (564*a*, 564*b*, 564*c*) is/are configured such that the filter's suppression such as the suppression of electromagnetic interference may be improved or increased.

44. The electronic module (500) according to any of items 41 to 43,
characterized in that
the resistor (570) is a series resistor (570) and/or the inductor (575) is a series inductor (575) and/or the capacitor (564*a*, 564*b*, 564*c*) is a parallel capacitor (564*a*, 564*b*, 564*c*).

45. A lead (300) for neural stimulation comprising at least one electronic module (500) for a system for neural applications (100) according to any of items 1 to 44.

46. A controller (110) comprising at least one electronic module (500) for a system for neural applications (100) according to any of items 1 to 44.

47. The controller (110) according to item 46,
characterized in that
the controller (110) is an implantable pulse generator (110).

48. An active lead can element (111) comprising at least one electronic module for a system for neural applications (100) according to any of items 1 to 44.

49. A system for neural applications (100) comprising at least one electronic module (500) for a system for neural applications (100) according to any of items 1 to 44 and/or comprising at least one lead (300) according to item 45 and/or comprising at least one controller (110) according to item 47 and/or comprising at least one active lead can element (111) according to item 48.

50. An electronic module (500) or a lead (300) or a controller (110) or an active lead can element (111) or a system (100) according to one of the preceding items,
characterized in that
the system is a neurostimulation and/or neurorecording system (100).

51. An electronic module (500) or a lead (300) or a controller (110) or an active lead can element (111) or a system (100) according to one of the preceding items
characterized in that
the system (100) is a deep brain stimulation (DBS) system (100).

The invention claimed is:

1. A medical device comprising:
a non-conductive layer having a first side and a second side;
two or more electrical contacts adjacent the first side of the non-conductive layer;
a conductive layer having a first side and a second side, the first side of the conductive layer adjacent the second side of the non-conductive layer, the conductive layer electrically isolated from each of the two or more electrical contacts;
a semiconductive substrate adjacent the second side of the conductive layer;
two or more DC blocking capacitors mounted on the substrate;
two or more feedthrough pins extending through, but electrically isolated from, the conductive layer, each of the feedthrough pins being electrically coupled to a respective one of the two or more electrical contacts;
a plurality of electrodes, each of the plurality of electrodes electrically coupled to a respective one of the two or more electrical contacts, wherein each of the two or more electrical contacts forms, with the conductive layer, a respective filter capacitor configured to filter a signal received by the electrical contact, and each of the two or more feedthrough pins extends through the substrate and is electrically coupled to a respective one of the two or more DC blocking capacitors; and
a housing configured to at least partially house the non-conductive layer, the two or more electrical contacts, the conductive layer, the two or more feedthrough pins, and an integrated circuit configured to receive the signals filtered by the filter capacitors, wherein at least a portion of the housing is conductive, the conductive layer is electrically coupled to the conductive portion of the housing, and the housing has an overall thickness of less than 10 millimeters.

2. The medical device of claim 1, further comprising two or more feedthrough vias, each of the two or more feedthrough vias carrying a respective one of the two or more feedthrough pins,
wherein each of the two or more feedthrough vias defines an opening in the conductive layer, and
wherein each of the two or more electrical contacts at least partially covers the opening in the conductive layer defined by a respective one of the two or more feedthrough vias.

3. The medical device of claim 2, wherein each of the two or more electrical contacts covers the opening in the conductive layer defined by a respective one of the two or more feedthrough vias.

4. The medical device of claim 1, further comprising a housing configured to at least partially house the non-conductive layer, the two or more electrical contacts, the conductive layer, the two or more feedthrough pins, and an integrated circuit configured to receive the signals filtered by the filter capacitors, wherein at least a portion of the housing is conductive, and wherein the conductive layer is electrically coupled to the conductive portion of the housing.

5. The medical device of claim 1, wherein the conductive layer is configured as a ground plane for the medical device.

6. The medical device of claim 1, wherein the substrate has a plurality of sides and the conductive layer at least partially wraps around the sides of the substrate.

7. The medical device of claim 1, further comprising an integrated circuit coupled to receive the signals filtered by the filter capacitors from the two or more feedthrough pins via the DC blocking capacitors.

8. The medical device of claim 1, wherein each of the two or more electrical contacts is electrically coupled to a respective one of two or more connector pins of at least one multi-pin connector.

9. The medical device of claim 1, further comprising a plurality of inductors, each of the plurality of inductors configured in parallel or in series with a respective one of the filter capacitors.

10. The medical device of claim 1, wherein the housing has an overall thickness of less than 4 millimeters.

11. The medical device of claim 1, wherein the housing has a length of about 20 millimeters, a width of about 10 millimeters, and wherein the two or more electrical contacts form a high-count feed-through (HCFX) connector.

12. The medical device of claim 11,
wherein the two or more electrical contacts comprise about 40 electrical contacts that form the HCFX connector.

13. A medical device comprising:
a plurality of electrodes;
a plurality of connector pins of at least one multi-pin connector, each of the plurality of connector pins electrically coupled to a respective one of the plurality of electrodes;
an integrated feedthrough filter array comprising:
  a non-conductive layer having a first side and a second side;
  two or more electrical contacts adjacent the first side of the non-conductive layer, each of the two or more electrical contacts electrically coupled to a respective one of the plurality of electrodes via a respective one of the plurality of connector pins;
  a conductive layer having a first side and a second side, the first side of the conductive layer adjacent the second side of the non-conductive layer, the conductive layer electrically isolated from each of the two or more electrical contacts;
  a semiconductive substrate adjacent the second side of the conductive layer;
  two or more DC blocking capacitors mounted on the substrate;
  two or more feedthrough pins extending through, but electrically isolated from, the conductive layer, each of the feedthrough pins being electrically coupled to a respective one of the two or more electrical contacts, wherein each of the two or more electrical contacts forms, with the conductive layer, a respective filter capacitor configured to filter a signal received by the electrical contact, wherein each of the two or more feedthrough pins extends through the substrate and is electrically coupled to a respective one of the two or more DC blocking capacitors; and
  two or more feedthrough vias, each of the two or more feedthrough vias carrying a respective one of the two or more feedthrough pins, wherein each of the two or more feedthrough vias defines an opening in the conductive layer, and wherein each of the two or more electrical contacts covers the opening in the conductive layer defined by a respective one of the two or more feedthrough vias; and
an integrated circuit electrically coupled to receive the signals filtered by the filter capacitors from the two or more feedthrough pins via the DC blocking capacitors, wherein the integrated circuit is configured to:
  provide a therapy signal to a patient via at least one of the two or more electrical contacts and the respective at least one of the plurality of electrodes; and
  receive a sensed signal from the patient via at least one of the plurality of electrodes and the respective at least one of the two or more electrical contacts; and
a housing configured to at least partially house the integrated feed-through filter and the integrated circuit, wherein at least a portion of the housing is conductive, the plurality of connector pins of the at least one multi-pin connector extend through the housing, the conductive layer of the integrated feed-through filter is electrically coupled to the conductive portion of the housing, and the housing has an overall thickness of less than 10 millimeters.

14. The medical device of claim 13, wherein the conductive layer is configured as a ground plane for the medical device.

15. The medical device of claim 13, wherein the substrate carries the conductive layer on a plurality of sides of the substrate.

16. A medical device comprising:
a non-conductive layer having a first side and a second side, wherein the non-conductive layer comprises a high-k dielectric material;
two or more electrical contacts adjacent the first side of the non-conductive layer;
a conductive layer adjacent the second side of the non-conductive layer and electrically isolated from each of the two or more electrical contacts;
a substrate carrying the conductive layer;
two or more DC blocking capacitors; and
two or more feedthrough pins extending through, but electrically isolated from, the conductive layer, each of the feedthrough pins being electrically coupled to a respective one of the two or more electrical contacts,
wherein each of the two or more electrical contacts forms, with the conductive layer, a respective filter capacitor configured to filter a signal received by the electrical contact, and
wherein each of the two or more feedthrough pins extends through the substrate and is electrically coupled to a respective one of the two or more DC blocking capacitors.

17. A medical device comprising:
a plurality of electrodes;
a plurality of connector pins of at least one multi-pin connector, each of the plurality of connector pins electrically coupled to a respective one of the plurality of electrodes;
two or more DC blocking capacitors;
an integrated feedthrough filter array comprising:
  non-conductive layer having a first side and a second side, wherein the non-conductive layer comprises a high-k dielectric material;
  two or more electrical contacts adjacent the first side of the non-conductive layer, each of the two or more electrical contacts electrically coupled to a respective one of the plurality of electrodes via a respective one of the plurality of connector pins;
  a conductive layer adjacent the second side of the non-conductive layer and electrically isolated from each of the two or more electrical contacts;
  a substrate carrying the conductive layer; and
  two or more feedthrough pins extending through, but electrically isolated from, the conductive layer, each of the feedthrough pins being electrically coupled to a respective one of the two or more electrical contacts, wherein each of the two or more electrical contacts forms, with the conductive layer, a respective filter capacitor configured to filter a signal received by the electrical contact, wherein each of the two or more feedthrough pins extends through the substrate and is electrically coupled to a respective one of the two or more feedthrough vias;
an integrated circuit electrically coupled to receive the signals filtered by the filter capacitors from the two or more feedthrough pins via the DC blocking capacitors, wherein the integrated circuit is configured to at least one of:
provide a therapy signal to a patient via at least one of the two or more electrical contacts and the respective at least one of the plurality of electrodes; or
receive a sensed signal from the patient via at least one of the plurality of electrodes and the respective at least one of the two or more electrical contacts; and
a housing configured to at least partially house the integrated feed-through filter and the integrated circuit, wherein at least a portion of the housing is conductive, wherein the plurality of connector pins of the at least one multi-pin connector extend through the housing, and wherein the conductive layer of the integrated feed-through filter is electrically coupled to the conductive portion of the housing.

* * * * *